United States Patent [19]

Schaper et al.

[11] Patent Number: 4,717,724

[45] Date of Patent: Jan. 5, 1988

[54] 1-(1,3-DIOXOLAN-2-YLMETHYL)AZOLES, THEIR SALTS AND THEIR USE

[75] Inventors: Wolfgang Schaper, Frankfurt am Main; Ernst Blume, Bad Soden am Taunus; Wolfgang Raether, Dreieich; Walter Dittmar, Hofheim am Taunus, all of Fed. Rep. of Germany

[73] Assignee: Hoechst Aktiengesellschaft, Frankfurt, Fed. Rep. of Germany

[21] Appl. No.: 587,585

[22] Filed: Mar. 8, 1984

[30] Foreign Application Priority Data

Mar. 10, 1983 [DE] Fed. Rep. of Germany ....... 3308554

[51] Int. Cl.$^4$ ..................... A61K 31/47; C07D 401/14
[52] U.S. Cl. .................................... 514/278; 514/307; 546/18; 546/144; 546/148
[58] Field of Search .................... 546/18, 144, 148; 514/278, 307

[56] References Cited

U.S. PATENT DOCUMENTS

| | | | |
|---|---|---|---|
| 3,583,994 | 7/1971 | Mathison | 546/148 |
| 3,936,470 | 2/1976 | Heeres | 260/309 |

FOREIGN PATENT DOCUMENTS

| | | |
|---|---|---|
| 837831 | 3/1976 | Belgium . |
| 50298 | 4/1982 | European Pat. Off. . |
| 51190 | 5/1982 | European Pat. Off. . |
| 0006712 | 2/1983 | European Pat. Off. . |
| 94052 | 6/1983 | European Pat. Off. . |
| 0006722 | 4/1984 | European Pat. Off. . |
| 0052905 | 6/1984 | European Pat. Off. . |
| 2803870 | 8/1978 | Fed. Rep. of Germany . |
| 2804096 | 9/1978 | Fed. Rep. of Germany . |
| 2428046 | 1/1980 | France . |

OTHER PUBLICATIONS

Chemical Abstracts, vol. 84, 1976, p. 8, ref. 25713g.
*Organicum*, Veb. Deutscher Verlag Der Wisenschaften, Berlin, 1977, p. 542.
Borch et al., *J.A.C.S.*, 1971, pp. 2897–2904.
Marchini et al., *J. Org. Chem.*, 1975, pp. 3453–3456.
Gribble et al., *Synthesis*, 1975, pp. 650–652.
Woodward et al., *J. Amer. Chem. Soc.*, 67, 1945, pp. 860–874.
Robinson, *J. Amer. Chem. Soc.*, 69, 1947, pp. 1944–1945.
Georgian et al., *J. Org. Chem.*, 27, 1962, pp. 4571–4579.
Buck, *J. Amer. Chem. Soc.*, 56, 1934, pp. 1769–1771.
Kametani et al., *J. Chem. Soc.*, ©, 1971, pp. 2632–2634.
Kamatani et al., *J. Chem. Soc. Jap.*, 89, 1969, pp. 1482–1487.
Teitel et al., *J. Heterocyclic Chem.*, 5, 1968, pp. 825–829.
Whaley et al., *Org. Reactions*, vol. 6, New York, 1951, pp. 74–150.
Elderfield, *Heterocyclic Compounds*, vol. 4, p. 399.
Heeres et al., *J. Med. Chem.*, 22, 1979, pp. 1003–1005.

*Primary Examiner*—Glennon H. Hollrah
*Assistant Examiner*—James H. Turnipseed
*Attorney, Agent, or Firm*—Finnegan, Henderson, Farabow, Garrett & Dunner

[57] ABSTRACT

New 1-(1,3-dioxolan-2-ylmethyl)azoles, their stereoisomers and their salts are described, as are processes for their preparation. The new compounds are chemotherapeutic agents. They are active against skin fungi, mold fungi and yeasts and against bacteria.

3 Claims, No Drawings

1-(1,3-DIOXOLAN-2-YLMETHYL)AZOLES, THEIR SALTS AND THEIR USE

The invention relates to the subject matter comprised in the claims.

1-(1,3-Dioxolan-2-ylmethyl)-1H-imidazoles and -1H-1,2,4-triazoles for controlling fungi and bacteria are disclosed in U.S. Pat. No. 3,936,470, French Pat. No. 2,428,046, German Pat. Nos. 2,803,870 and 2,804,096 and European Pat. Nos. 0,006,712, 0,006,722, 0,050,298 and 0,052,905; however, their activity and tolerability are not always entirely satisfactory. The compounds according to the invention differ from these compounds essentially in the nature of the substituents in the 4-position of the dioxolane group and in improved and broader-spectrum antimycotic efficacy and improved tolerability.

In the following text, the term "$C_1$-$C_4$-alkyl" is to be understood to be an unbranched or branched hydrocarbon radical having 1-4 carbon atoms, such as, for example, the methyl, ethyl, propyl, 1-methylethyl, 2-methylpropyl or 1,1-dimethylethyl radical, the term "$C_1$-$C_{12}$-alkyl" is to be understood to be an unbranched or branched hydrocarbon radical having 1-12 carbon atoms, such as, for example, the abovementioned radicals or the pentyl, hexyl, heptyl, octyl, nonyl, decyl, undecyl, dodecyl or 1,1-dimethyl-3,3-dimethylbutyl radical, the term "$C_3$-$C_8$-cycloalkyl" is to be understood to be an unbranched cyclic hydrocarbon radical having 3-8 carbon atoms, such as, for example, the cyclopropyl, cyclopentyl, cyclohexyl, cycloheptyl or cyclooctyl radical, the term "$C_1$-$C_4$-alkoxy" is to be understood to be an alkoxy group the hydrocarbon radical of which has the meaning indicated under the term "$C_1$-$C_4$-alkyl", the term "$C_1$-$C_4$-dialkylamino" is to be understood to be a dialkylamino group having identical or different hydrocarbon radicals, these having the meaning indicated under the term "$C_1$-$C_4$-alkyl", the two alkyl groups being separate or forming a pyrrolidine, piperidine or hexamethylene-imine ring together with the nitrogen atom to which they are affixed, the term "$C_1$-$C_5$-alkanoyl" is to be understood to be an unbranched or branched alkanoyl radical having 1-5 carbon atoms, such as the formyl, acetyl, propanoyl, 2-methylpropanoyl, butanoyl, pentanoyl and 2,2-dimethylpropanoyl group, the term "$C_3$-$C_5$-alkenyl" is to be understood to be a branched or unbranched alkene radical having 3-5 carbon atoms, such as, for example, the 2-propenyl, 2-butenyl or 2-pentenyl group, the term "$C_3$-$_5$-alkinyl" is to be understood to be an unbranched or branched alkine radical having 3-5 carbon atoms, such as, for example, the 2-propinyl, 2-butinyl or the 2-pentinyl group, the term "$C_1$-$C_4$-alkylthio" is to be understood to be an alkylthio group the hydrocarbon radical of which has the meaning indicated under the term "$C_1$-$C_4$-alkyl", the term "aryl group" is to be understood to be the phenyl, naphthyl or biphenylyl group, the term "heteroaryl group" is to be understood to be a heteroaromatic system having 5 or 6 ring members, preferably thiophene, furan or pyridine, the terms "$C_1$-$C_5$-arylalkyl group" and "$C_1$-$C_5$-heteroarylalkyl group" are to be understood to be a branched or, preferably, unbranched arylalkyl or heteroarylalkyl radical having 1-5 carbon atoms in the alkyl moiety, "aryl" and "heteroaryl" having the meanings indicated above, such as, for example, the benzyl, 2-phenylethyl, 3-phenylpropyl, 4-phenylbutyl, 5-phenylpentyl, 2-thienylmethyl, 3-thienylmethyl, 4-pyridylmethyl, 2-(2-thienyl)ethyl, 3-(2-thienyl)propyl, 2-(3-thienyl)ethyl, 4-biphenylylmethyl, 2-(4-biphenylyl)ethyl, 1-naphthylmethyl and 2-naphthylmethyl group, and the term "halogen" is to be understood to be a fluorine, chlorine, bromine or iodine atom.

The invention relates to 1-(1,3-dioxolan-2-ylmethyl)azoles of the general formula (I)

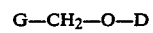

G—CH$_2$—O—D  (I)

and their stereoisomers and their salts with physiologically tolerated acids, in which G denotes a 1-(1,3-dioxolan-2-ylmethyl)azole radical of the structure below,

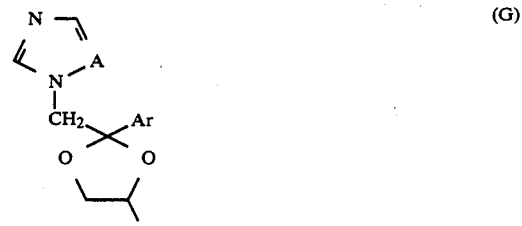

(G)

in which A denotes nitrogen or methine, Ar denotes naphthyl, biphenylyl, thienyl, or a phenyl group which optionally bears one, two or three substituents, the substituents being identical or different and denoting halogen, trifluoromethyl, $C_1$-$C_4$-alkyl or $C_1$-$C_4$-alkoxy, and D in formula (I) either 1.1 denotes an isoquinoline group of the formula D I

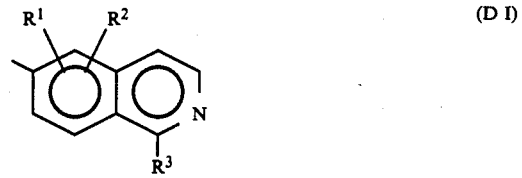

(D I)

where $R^1$ and $R^2$, independently of one another, denote a hydrogen atom, halogen, $C_1$-$C_4$-alkyl or $C_1$-$C_4$-alkoxy, and $R^3$ denotes a hydrogen atom, $C_1$-$C_{12}$-alkyl, $C_3$-$C_8$-cycloalkyl, $C_3$-$C_5$-alkenyl, $C_3$-$C_5$-alkinyl, trifluoromethyl, trichloromethyl, heteroaryl, $C_1$-$C_5$-heteroarylalkyl, or an aryl or $C_1$-$C_5$-arylalkyl group which optionally bears one, two or three substituents, the substituents on the aryl group being identical or different and each denoting halogen, nitro, $C_1$-$C_4$-alkyl, trifluoromethyl, $C_1$-$C_4$-alkoxy, $C_1$-$C_4$-alkylthio, $C_1$-$C_4$-dialkylamino, phenylthio, halogenophenylthio, phenoxy or halogenophenoxy, or 1.2. denotes a 3,4-dihydroisoquinoline group of the formula D II

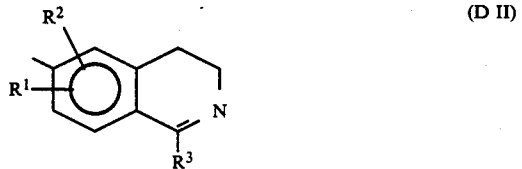

(D II)

where $R^1$, $R^2$ and $R^3$ have the meanings indicated for formula DI, or 1.3. denotes a 1,2,3,4-tetrahydroisoquinoline group of the formula D III

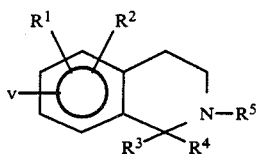

where v indicates the position of linkage of the isoquinoline system to the G—CH$_2$—O radical, R$^1$, R$^2$ and R$^3$ have the meanings indicated for formula D I, and R$^4$ denotes a hydrogen atom or a C$_1$–C$_4$-alkyl group, and additionally, if R$^3$ and R$^4$ are alkyl groups, these, together with the carbon atom bearing them, can denote a spirocyclic ring system of the general formula D III',

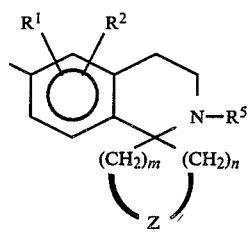

in which m and n denote 1, 2 or 3, and Z denotes either a methylene group or, if m=n=2, a heteroatom from the group comprising oxygen, sulfur or nitrogen, it being possible for the nitrogen to be substituted by a radical R$^6$ which denotes C$_1$–C$_4$-alkyl, C$_1$–C$_5$-alkanoyl, C$_1$–C$_4$-alkoxycarbonyl, or a benzoyl or benzyl group which is optionally provided with one or two substituents, it being possible for the substituents on the phenyl ring to be identical or different and each denoting halogen, C$_1$–C$_4$-alkyl, trifluoromethyl or C$_1$–C$_4$-alkoxy and, when R$^3$ and/or R$^4$ is not a hydrogen atom, v denotes the 6-position, or, when R$^3$ and R$^4$ are hydrogen atoms, v denotes the 5-, 6-, 7- or 8-position, and, if R$^3$ and/or R$^4$ is not a hydrogen atom, R$^5$ denotes a hydrogen atom or a C$_1$–C$_4$-alkyl group, or, if R$^3$ and R$^4$ are hydrogen atoms and v denotes the 5-, 7- or 8-position, R$^5$ can have the meanings indicated for R$^3$ in formula D I, with the proviso that R$^5$ does not denote an aryl or heteroaryl group, or, when R$^3$ and R$^4$ are hydrogen atoms and v denotes the 6-position, R$^5$ has the meanings indicated for R$^3$ in formula D I, and R$^5$ can also denote an acyl group of the general formula Q, $$-\underset{\underset{O}{\|}}{C}-R^7 \qquad Q$$

where R$^7$ can have the meanings indicated for R$^3$ in the formula D I.

Preferred compounds of the formula (I) are those in which, in this formula, Ar denotes a phenyl group which is substituted by 1 or 2 halogen atoms, preferably fluorine, chlorine or bromine, a 4-trifluoromethylphenyl, 4-methylphenyl, 4-methoxyphenyl or a biphenylyl group, R$^1$ and R$^2$ are hydrogen atoms, and the linkage between the dioxolane and isoquinoline moieties in formula (I) is preferably at C$_6$ or C$_7$ of the isoquinoline moiety.

More highly preferred compounds of the general formula (I) are those in which Ar denotes the 4-chlorophenyl or the 2,4-dichlorophenyl group, R$^1$ and R$^2$ denote hydrogen atoms, the linkage between the dioxolane and isoquinoline moieties is at C$_6$ or C$_7$ of the isoquinoline moiety, and the radical D in formula (I) is a tetrahydroisoquinoline derivative of the general formula (D III).

The most preferred compounds of the general formula (I) are those in which A denotes a methine group, Ar denotes a 2,4-dichlorophenyl group, and the radical D is a tetrahydroisoquinoline of the general formula (D III) in which R$^1$, R$^2$, R$^3$ and R$^4$ denote hydrogen atoms, and R$^5$ denotes a C$_1$–C$_4$-arylalkyl group, and which is bonded to the dioxolane radical in formula (I) via C$_6$ or C$_7$ of the isoquinoline system.

The invention also relates to a process for the preparation of the compounds of the general formula (I) in claim 1, which comprises (a) reacting a compound of the general formula (II)

$$G-CH_2-E \qquad (II)$$

in which E denotes halogen or a reactive ester radical, with a compound of the general formula (III)

$$H-O-D \qquad (III)$$

in which D has the meaning indicated in claim 1, and, where appropriate, acylating, alkylating or reducing a compound of the formula (I) thus obtained, or (b) first reacting a compound of the general formula (IV)

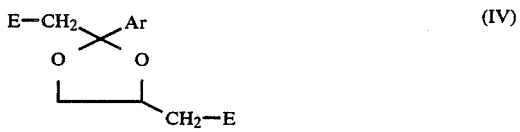

in which Ar has the meanings indicated in claim 1 for formula I, and E has the meanings indicated for formula (II), with a compound of the general formula III and thus preparing a compound of the general formula (V)

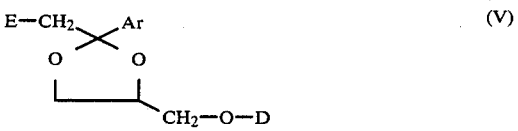

in which Ar and D have the meanings indicated in claim 1, and E has the meanings indicated for formula (II) in claim 2, and then reacting the compound of the general formula (V) thus obtained with a compound of the general formula (VI)

in which A has the meanings indicated in claim 1, and Me denotes hydrogen or a metal atom, and, where appropriate, acylating, alkylating or reducing a compound of the formula (I) thus obtained, and, where appropriate, converting a compound obtained according to (a) or (b) into the salt with a physiologically tolerated acid.

In process variant (a) in accordance with the following equation, the compounds of the general formula (I) are prepared by reacting an appropriately substituted isoquinoline of the general formula (III) with a compound of the general formula (II)

where G in the abovementioned general formula (II) has the meaning indicated for formula (I) in claim 1, and E denotes a reactive leaving group, such as chlorine, bromine, iodine or trifluoroacetyloxy, or a sulfonyloxy group, such as, for example, methylsulfonyloxy, 4-methylphenylsulfonyloxy, 4-chlorophenylsulfonyloxy or trifluoromethylsulfonyloxy, and D has the meanings indicated for formula I.

The abovementioned reaction is carried out in a temperature range from 30° to 150° C., preferably 40° to 100° C., advantageously in the presence of a base and in an inert organic solvent, such as N,N-dimethylformamide, N,N-dimethylacetamide, dimethyl sulfoxide, N-methyl-2-pyrrolidone, dioxane, tetrahydrofuran, 4-methyl-2-pentanone, methanol, ethanol, isopropyl alcohol, propanol, butanol, pentanol, tert.-butyl alcohol, methylglycol, methylene chloride or an aromatic hydrocarbon, such as benzene, chlorobenzene, toluene or xylene, or in water. It is also possible to use mixtures of the solvents mentioned as examples.

Examples of suitable bases are alkali metal or alkaline earth metal carbonates, bicarbonates, hydroxides, alcoholates or hydrides, such as, for example, sodium carbonate, sodium bicarbonate, potassium carbonate, sodium hydroxide, sodium methylate or sodium hydride.

The reaction likewise takes place under the conditions of a phase-transfer reaction, by allowing the reactants to act on one another in an aromatic hydrocarbon, such as benzene, chlorobenzene, toluene or xylene, with vigorous stirring in the presence of a phase-transfer catalyst and either a powdered alkali metal hydroxide, such as, for example, sodium or potassium hydroxide, or a concentrated aqueous solution of the same, preferably in a temperature range from 20° to 120° C.

Examples of suitable phase-transfer catalysts are trialkylbenzylammonium or tetraalkylammonium halides, hydroxides, or bisulfates, preferably having 1 to 12 carbon atoms in the alkyl radical, or crown ethers, such as, for example, 12-crown-4, 15-crown-5, 18-crown-6 or dibenzo-18-crown-6.

Those compounds of the general formula (I) in which the radical D denotes the radical D III can also be prepared by first reacting a compound of the general formula (II) with a compound of the general formula (IIIa) in which $R^1$, $R^2$, $R^3$ and $R^4$ have the meanings indicated in claim 1, and in which a hydrogen atom is present in place of $R^5$ in formula D III in claim 1.3, alkylating the compound of the general formula (Ia) thus obtained, in which $R^1$, $R^2$, $R^3$ and $R^4$ have the meanings indicated above,

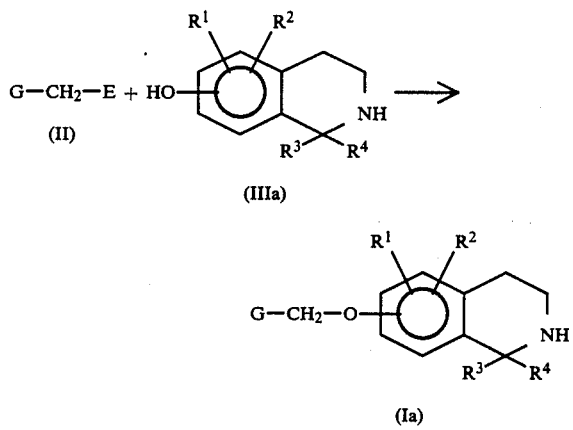

with an alkylating agent Alk-E, to give a compound of the general formula (Ib), or acylating, with an acylating agent $R^7$—CO—X, to give a compound of the general formula (Ic) and, where appropriate, reducing (Ic) to give (Ib),

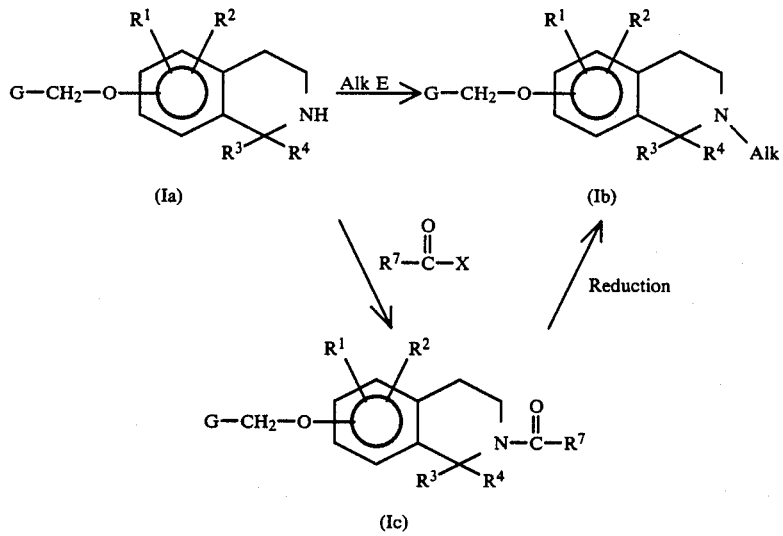

where Alk denotes $C_1$–$C_{12}$-alkyl, $C_3$–$C_8$-cycloalkyl, $C_3$–$C_5$-alkenyl, $C_3$–$C_5$-alkinyl, $C_1$–$C_5$-heteroarylalkyl or $C_1$–$C_5$-arylalkyl, it being possible for the aryl group to bear one, two or three substituents, these substituents being identical or different and each denoting halogen, nitro, $C_1$–$C_4$-alkyl, trifluoromethyl, $C_1$–$C_4$-alkoxy, $C_1$–$C_4$-alkylthio, $C_1$–$C_4$-dialkylamino, phenylthio, halogenophenylthio, phenoxy or halogenophenoxy, and E denotes a reactive leaving group, such as chlorine, bromine, iodine, trifluoroacetyloxy or a sulfonyloxy group, such as methylsulfonyloxy, phenylsulfonyloxy, 4-methylphenylsulfonyloxy, 4-chlorophenylsulfonyloxy or trifluoromethylsulfonyloxy, $R^7$ has the meanings indicated for formula I, and X denotes chlorine, bromine, iodine, $C_1$–$C_4$-alkoxy, aryloxy or aryl-$C_1$–$C_4$-alkoxy, or a group of the formula

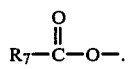

It is advantageous for the reaction of the compounds (II) and (IIIa) to add a suitable base to a compound (IIIa) in an inert dipolar aprotic organic solvent, such as dimethylformamide, dimethylacetamide, tetramethylurea, sulfolane or dimethyl sulfoxide, and then to stir the mixture with a compound (II) at a temperature between 20° and 120° C. for one or more hours.

In this context, examples of suitable bases are alkali metal or alkaline earth metal amides or hydrides.

The subsequent alkylation of the compounds of the general formula (Ia) with Alk-E is advantageously carried out in an inert organic solvent in the presence of a suitable base at a temperature between 20° and 120° C. In this context, examples of suitable bases are alkali metal or alkaline earth metal carbonates or bicarbonates.

The alkylations of the OH and then of the NH group which are described above as carried out stepwise are advantageously carried out as a one-pot reaction by first reacting a compound of the general formula (IIIa) at 20° to 120° C. with a compound of the general formula (II), in the presence of one equivalent of a base mentioned above for the first alkylation step, in one of the above-mentioned inert solvents, and then, without isolating the compound (Ia), adding the alkylating agent Alk-E and one equivalent of a base mentioned for the second alkylation step, and again heating to a temperature between 20° and 120° C.

Depending on the accessibility of the starting materials, the conversion of compounds of the general formula (Ia) into products of alkylation of the general formula (Ib) can also be carried out by reacting a compound (Ia) with a carbonyl compound in the presence of a reducing agent in an inert solvent (reductive amination).

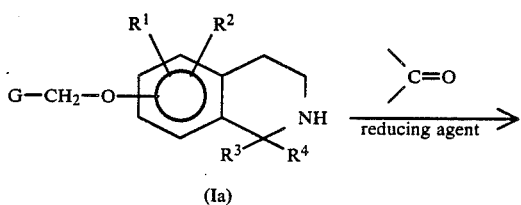

(Ia)

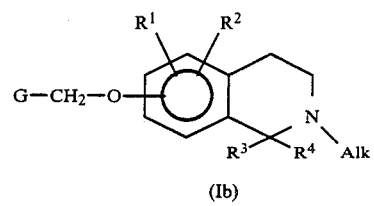

(Ib)

Examples of combinations of carbonyl compounds and reducing agents suitable for this purpose are aldehydes or ketones and hydrogen in the presence of a metal catalyst, such as, for example, Raney nickel under elevated pressure (Organikum, VEB Deutscher Verlag der Wissenschaften, Berlin 1977, page 542); aldehydes or ketones and sodium cyanoborohydride (J. Amer. Chem. Soc. 93, 2897, (1971); or carboxylic acids and sodium borohydride (J. Org. Chem. 40, 3453 (1975) and Synthesis 1975, 650).

For the preparation of the compounds of the formula (Ic), a compound of the general formula (Ia) is reacted with an acylating agent of the formula

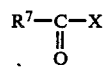

in an inert solvent, such as methylene chloride, chloroform, benzene, toluene or pyridine, advantageously in the presence of a base, such as an alkali metal or alkaline earth metal carbonate or bicarbonate, for example sodium carbonate, sodium bicarbonate or potassium carbonate, or an organic base, for example triethylamine, tributylamine, N-ethylmorpholine, pyridine, quinoline or 1H-imidazole.

The reduction of the compounds of the general formula (Ic) to give compounds of the general formula (Ib) is carried out with a complex metal hydride, such as lithium aluminum hydride, diisobutylaluminum hydride or sodium bis(2-methoxyethoxy)aluminum dihydride, in an inert solvent, such as diethyl ether, tetrahydrofuran, dioxane or dimethoxyethane, in a temperature range of 0°–50° C.

To carry out the process according to process variant (b), a compound of the general formula (IV)

(IV)

in which Ar has the meanings indicated in claim 1, and E has, in each case, one or several of the meanings indicated for E in formula (II), is first reacted with a compound of the general formula (III) in claim 2, and thus is prepared a compound of the general formula (V) in which Ar and D have the meanings indicated in claim 1, and E has the meanings indicated for formula (II) in claim 2.

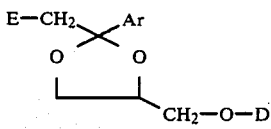

The reaction conditions for the preparation of the compounds of the general formula (V) by reacting compounds of the general formula (IV) with compounds of the general formula (III) are the same as indicated in process variant (a) for the reaction of compounds of the general formula (II) with (III).

The compound of the general formula (V) thus obtained is then reacted with a compound of the general formula (VI)

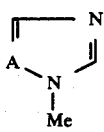

in which A has the meaning indicated in claim 1, and Me denotes hydrogen or a metal atom, preferably an alkali metal or alkaline earth metal atom.

The preparation of compounds of the general formula (I) by process variant (b) by reacting a compound of the general formula (V) with a compound of the general formula (VI) is advantageously carried out in an inert solvent and, where appropriate, in the presence of a base as indicated above for the first preparation process for the reaction of (II) with (III), preferably at a temperature between 100° and 190° C. Where appropriate, the reaction is carried out in an autoclave under pressure.

The reactions of (III) with (IV) to give (V) and then with (VI) to give (I) which are described above are advantageously carried out as a one-pot reaction by first reacting a compound of the general formula (IV) with a compound of the general formula (III) in the presence of one equivalent of a base in an inert solvent at 30° to 150° C. Then, without isolating the compound of the general formula (V), a compound of the general formula (VI) and a further equivalent of a base are added and the mixture is heated to 100° to 190° C.

The invention also relates to the compounds of the general formula (III') used as starting materials in the processes described above

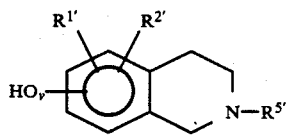

where v indicates the position of the hydroxyl group on the isoquinoline system and denotes the 5-, 6-, 7- or 8-position, and in which $R^{1'}$ and $R^{2'}$, independently of one another, denote a hydrogen atom, halogen or $C_1-C_4$-alkyl, and $R^{5'}$ denotes $C_5-C_{12}$-alkyl, $C_3-C_8$-cycloalkyl, $C_3-C_5$-alkenyl, $C_3-C_5$-alkinyl, trifluoromethyl, trichloromethyl, $C_1-C_5$-heteroarylalkyl, $C_1-C_5$-arylalkyl or, if v denotes the 6-position, also denotes aryl or heteroaryl, it being possible for the aryl groups in the aryl or $C_1-C_5$-arylalkyl groups to bear one, two or three substituents, these substituents being identical or different and each denoting halogen, nitro, $C_1-C_4$-alkyl, trifluoromethyl, $C_1-C_4$-alkoxy, $C_1-C_4$-alkylthio, $C_1-C_4$-dialkylamino, phenylthio, halogenophenylthio, phenoxy or halogenophenoxy, and in which $R^{5'}$ also denotes an acyl group of the general formula Q'

in which $R^{7'}$ denotes $C_5-C_{12}$-alkyl, $C_3-C_8$-cycloalkyl, $C_3-C_5$-alkenyl, $C_3-C_5$-alkinyl, trifluoromethyl, trichloromethyl, $C_1-C_5$-heteroarylalkyl, $C_1-C_5$-arylalkyl, aryl or heteroaryl, it being possible for the aryl groups in the aryl or $C_1-C_5$-arylalkyl groups to bear one, two or three substituents, these substituents being identical or different and each denoting halogen, nitro, $C_1-C_4$-alkyl, trifluoromethyl, $C_1-C_4$-alkoxy, $C_1-C_4$-alkylthio, $C_1-C_4$-dialkylamino, phenylthio, halogenophenylthio, phenoxy or halogenophenoxy.

The invention also relates to a process for the preparation of compounds of the general formula (III'a)

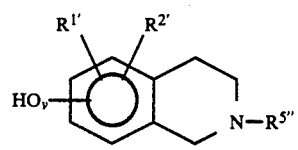

in which $R^{1'}$, $R^{2'}$ and v have the meanings indicated for formula (III'), and $R^{5''}$ denotes $C_5-C_{12}$-alkyl, $C_3-C_8$-cycloalkyl, $C_3-C_5$-alkenyl, $C_3-C_5$-alkinyl, trifluoromethyl, trichloromethyl, $C_1-C_5$-heteroarylalkyl or $C_1-C_5$-arylalkyl, it being possible for the aryl group to bear one,, two or three substituents, these substituents being identical or different and each denoting halogen, nitro, $C_1-C_4$-alkyl, trifluoromethyl, $C_1-C_4$-alkoxy, $C_1-C_4$-alkylthio, $C_1-C_4$-dialkylamino, phenylthio, halogenophenylthio, phenoxy or halogenophenoxy, which comprises reacting a compound of the general formula (III'g)

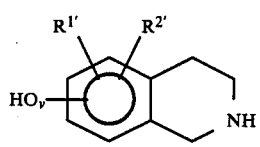

or a compound of the general formula (X)

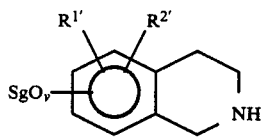

in which v, $R^{1'}$ and $R^{2'}$ have the meanings indicated above, and Sg denotes a protective group, such as a $C_1-C_4$-alkyl group, benzyl group or a group of the general formula

R⁷ having the meanings indicated for formula DIII, with an alkylating agent Alk'E, Alk' denoting C₅-C₁₂-alkyl, C₃-C₈-cycloalkyl, C₃-C₅-alkenyl, C₃-C₅-alkinyl, trifluoromethyl, trichloromethyl, C₁-C₅-heteroarylalkyl or C₁-C₅-arylalkyl, it being possible for the aryl group to bear one, two or three substituents, these substituents being identical or different and each denoting halogen, nitro, C₁-C₄-alkyl, trifluoromethyl, C₁-C₄-alkoxy, C₁-C₄-alkylthio, C₁-C₄-dialkylamino, phenylthio, halogenophenylthio, phenoxy or halogenophenoxy, and E denotes a reactive leaving group with the meanings indicated above, and the protective group Sg is split off from the compounds obtained from the compound of the formula (X).

The reaction is carried out under the conditions of an N-alkylation by reacting a compound (III'g) or (X) with the alkylating agent Alk-E in the presence of a suitable base, preferably an alkali metal or alkaline earth metal carbonate or bicarbonate, in an inert solvent, such as acetonitrile, dimethylformamide, dimethylacetamide, dimethyl sulfoxide, tetramethylurea or sulfolane, at a temperature between 20° and 120° C.

There is a large number of methods available for removing the various protective groups Sg from the intermediates of the general formula (X')

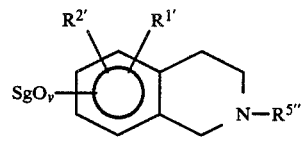

in which R¹', R²', R⁵' and Sg have the meanings indicated above (cf. T. W. Greene, Protective Groups in Organic Synthesis, New York 1981, pages 87 et seq.). The cleavage of the methyl ethers is preferably carried out by heating with strong acids, such as, for example, hydrobromic acid, and the benzyl ethers are preferably cleaved by hydrogenolysis in the presence of noble metal catalysts, such as, for example, palladium or platinum. The acyl protective group is preferably split off by hydrolysis with aqueous sodium hydroxide or potassium hydroxide solution or by heating with a dialkylamine, for example diethylamine, in an inert solvent, for example ethanol. The tetrahydroisoquinolines of the general formula (III'g) and (X) required for the syntheses described above are known (cf. for example J. Heterocyclic Chem. 8, 665 (1971) and Literature cited there), or can be prepared in analogy to known procedures.

The invention also relates to a process for the preparation of compounds of the general formula (III'b)

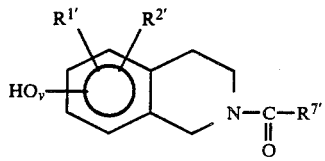

in which R¹', R²', v and R⁷' have the meanings indicated for formula (III'), which comprises reacting a compound of the general formula (III'g) or (X) with an acylating agent

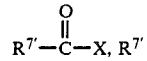

having the meanings indicated above and X denoting a reactive leaving group, such as halogen or a reactive ester radical, and in which the protective group Sg is split off from the compounds of the general formula (X'') obtained from the compound of the general formula (X)

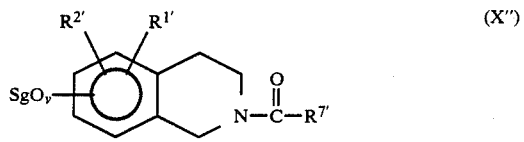

in which R¹', R²', R⁷', Sg and v have the meanings indicated above.

The reaction of the compounds (III'g) or (X) with the compounds

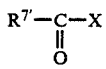

is carried out under the conditions of N-acylation according to the procedure already described for the preparation of the compounds of the general formula (Ic) from the compounds of the general formula (Ia).

The selected protective group is advantageously either the benzyl group, which is removed by hydrogenolysis as described above after acylation has been effected, or the

radical, R⁷' having the meanings indicated above, and the procedure is such that the compound of the general formula (III'g) is first O- and N-acylated in a customary manner with 2 equivalents of acylating agent R⁷'-COX in the presence of a base, and the protective group in the bisalkanoyl compound (X'') thus obtained, in which Sg denotes the group

is split off by heating with a dialkylamine, such as, for example, diethylamine, in an inert solvent, such as, for example, ethanol (cf. Tetrahedron Letters 1982, 1845).

The invention also relates to a process for the preparation of compounds of the general formula (III'c)

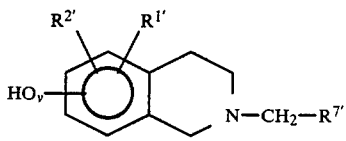

in which R¹', R²', R⁷'' and v have the meanings indicated for formula (III'), which comprises (a) reducing a compound of the general formula (III'b) or a compound of the general formula (X') with a complex metal hydride, and splitting off the protective group Sg from the compounds obtained from the compound (X''), or (b) reacting a compound of the general formula (III'g) or (X) with an aldehyde of the general formula R⁷'-CHO under the conditions of reductive amination, R⁷' having the meanings indicated above, and in which the protective group Sg is split off from the compounds obtained from the compound (X), or (c) reacting a compound of the general formula (III'd)

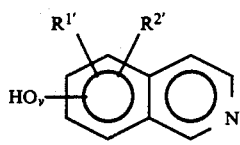
(III'd)

in which v, R¹' and R²' have the meanings indicated for formula (III'), with an alkylating agent Alk'E, Alk'E having the meanings indicated above, and reducing the compound of the general formula (XI) thus obtained

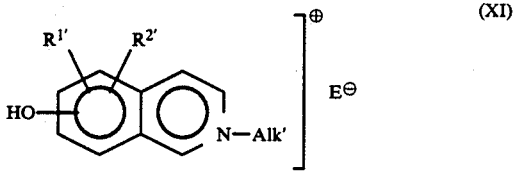
(XI)

in which v, R¹', R²' and Alk' have the meanings indicated above, with a complex hydride.

The reduction of the amides according to process variant (a) is carried out with the same reagents and under the same reaction conditions as described for the conversion of the compounds of the general formula (Ic) into compounds of the general formula (Ib).

The removal of a benzyl or alkyl protective group is carried out under the conditions indicated above.

The selected alkanoyl protective group is advantageously the

radical itself, R⁷' having the meanings indicated above, and the procedure is such that the compound of the general formula (III'g) is first O- and N-acylated in a customary manner with 2 equivalents of acylating agent R⁷'-COX in the presence of a suitable base, and the compounds of the general formula (III'c) are obtained from the bisalkanoyl compound thus obtained, by reduction with a complex metal hydride in an inert solvent (as described for the conversion of the compounds of the general formula (Ic) into compounds of the general formula (Ib)) the protective group being simultaneously split off.

For the preparation of the compounds (III'c) by process variant (b), an amine of the formula (III'g) or (X) is reacted with an aldehyde R⁷'-CHO under the conditions of reductive amination, as described above for the preparation of the compounds of the formula (Ib) from those of the formula (Ia). The reducing agents used are hydrogen in the presence of a metal catalyst, such as, for example, Raney nickel, or sodium cyanoborohydride.

A protective group is split off by the methods described above.

For the preparation of the compounds (III'c) by process variant (c), the hydroxyquinoline (III'd) is reacted with the alkylating agent Alk'-E in an inert solvent, such as ethanol, acetone or sulfolane, in a temperature range of 20°–150° C., preferably 50°–100° C., to give a compound of the general formula (XI), and the latter is reduced in a suitable solvent, such as water, methanol, ethanol or mixtures of these, using a suitable reducing agent, preferably sodium borohydride, to give the final products (III'c).

The hydroxyquinolines (III'd) are described in the literature or can be prepared in analogy to procedures known from the literature (cf. for example J. Amer. Chem. Soc. 67, 860 (1945); J. Amer. Chem. Soc, 69, 1944 (1947), J. Org. Chem. 27, 4571, (1962)).

The invention also relates to a process for the preparation of compounds of the general formula (III'e)

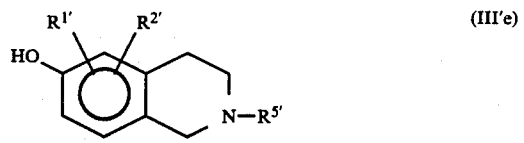
(III'e)

in which R¹', R²' and R⁵' have the meanings indicated for formula (III'), which comprises reacting a compound of the general formula (VII)

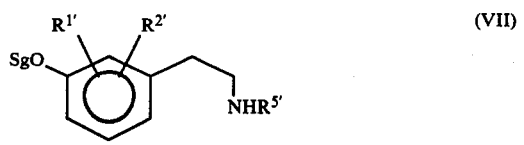
(VII)

in which R¹', R²', R⁵' and Sg have the meanings indicated for formula (III'), with formaldehyde in the presence of an acid, and then splitting off the group Sg.

To carry out this process, phenylethylamines of the general formula (XII) or phenylacetic acids of the general formula (XIII)

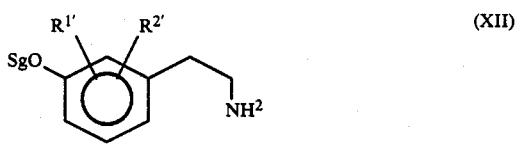
(XII)

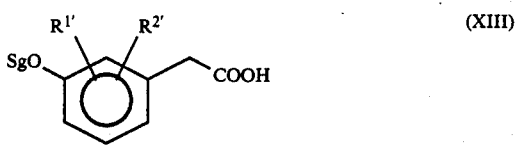
(XIII)

in which R¹', R²' and Sg have the meanings indicated above, are converted into the phenylethylamines (VII) by methods generally known (for example acylation/lithium alanate reduction; reductive amination), and the latter are converted by a Pictet-Spengler reaction, by heating the phenylethylamines (VII) with aqueous formaldehyde in the presence of an acid (cf. J. Amer. Chem. Soc. 56, (1934)) followed by removal of the protective group (as described above), into the final products (III'e).

For the preparation of other starting materials, some of which are known and are 6-hydroxy-1,2,3,4-tetrahydroisoquinolines (IIIf) which are monosubstituted or disubstituted in the 1-position, phenolic cyclization is advantageously selected (cf. J. Chem. Soc. (C) 1971, 2632; J. Pharm. Soc. Jap. 89, 1482 (1969)), in which the 6-hydroxyphenylethylamines (VIII) are heated with an aldehyde or ketone of the general formula (IX) in an inert solvent, preferably ethanol, $R^1$, $R^2$, $R^3$, $R^4$ and $R^5$ having the meanings indicated above for formula I.

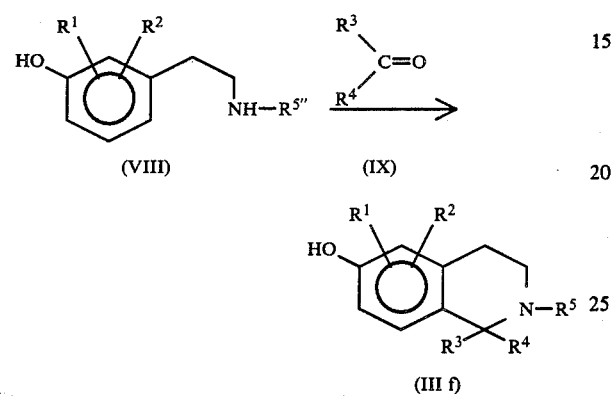

Some of the compounds of the general formula (III) in which D has the meaning D I or D II from formula (I), and other compounds in which D has the meaning D III from formula (I), are known, or they can be prepared in analogy to procedures in the literature (cf., for example J., Heterocyclic Chem. 5, 825 (1968); Org. Reactions Vol. 6, New York (1951), pages 74–150; R. C. Elderfield, Heterocyclic Compounds, Vol. 4, pages 399 et seq. and references cited there).

The preparation of starting compounds of the general formula (III) in which Ar has the meaning indicated for formula I and A denotes a methine group is described in Belgian Pat. No. 837,831, German Offenlegungsschrift No. 2,804,096 and J. Med. Chem. 22, 1003 (1979); those compounds in which A denotes nitrogen can be prepared in analogy to the literature references cited above.

The preparation of compounds of the general formula (IV) in which Ar has the meanings indicated for formula I, and E has the meanings indicated for formula (II), is described in European Pat. Nos. 0,050,298 and 0,052,905, or can be carried out in analogy to the literature references cited above.

The compounds of the general formula (I) also display their essential properties in the form of their salts. All physiologically tolerated acids are suitable for the preparation of acid addition salts. These preferably include the hydrogen halide acids, such as, for example, hydrochloric and hydrobromic acid, as well as nitric acid, and phosphoric acid or sulfuric acid. Preferred organic acids are monofunctional and bifunctional carboxylic acids and hydroxycarboxylic acids, such as, for example, acetic acid, maleic acid, oxalic acid, succinic acid, fumaric acid, tartaric acid, citric acid, salicylic acid, sorbic acid and lactic acid, and sulfonic acids, such as, for example, p-toluenesulfonic acid, methylsulfonic acid and phenylsulfonic acid and 1,5-napthalenedisulfonic acid. The salts of the compounds of the formula (I) can be obtained in a simple manner by customary methods of salt formation, for example by dissolving a compound of the formula (I) in a suitable inert solvent and adding the acid, for example hydrochloric acid or nitric acid, and can be isolated in a known manner, for example by filtration, and can, where appropriate, be purified by washing or recrystallization using an inert organic solvent.

It can be seen from the general formula (I) that the compounds according to the invention have at least two asymmetric carbon atoms located in the 2- and 4-positions of the dioxolane ring. Accordingly, these compounds can exist in the form of different stereoisomers.

The diastereomeric racemates (cis or trans form) of the compounds of the general formula (I) can be resolved in a customary manner. Examples of suitable methods are selective crystallization and chromatography, for example column chromatography.

Since the stereochemical configuration is already determined in the intermediates of the general formula (II) and (V), the separation into the cis and trans forms can be carried out even at this stage, or, preferably, yet earlier, for example at the stage of the intermediates of the general formula (IV). It is possible to carry out the separation readily by the methods described above. The cis and trans diastereomeric racemates can in turn be resolved in a customary manner into their optical antipodes cis(+), cis(−) and trans(+) and trans(−).

The new compounds of the formula (I) are chemotherapeutic agents and have an activity and tolerability for fungal infections which are superior relevant to those of known compounds, both on topical and on systemic administration. In vitro, they are very active against skin fungi, such as, for example, *Trichophyton mentagrophytes, Microsporum canis* and *Epidermophytes floccosum;* mold fungi, such as, for example, *Aspergillus niger*, or yeasts, such as, for example, *Candida albicans, C. tropicalis, Torulopsis glabrata* and *Trichosporon cutaneum* or *Trichomonas vaginalis* or *T. fetus,* or Gram-positive and Gram-negative bacteria.

The compounds also have a very good systemic effect, for example against *Candida albicans,* in vivo, for example on experimental candidosis of the mouse kidney, after oral or parenteral administration. Likewise, there is a very good effect on various pathogens of skin mycoses (for example *Trichophyton mentagrophytes*) of guineapigs after oral, parenteral or topical administration.

Examples of suitable forms for administration of the compounds according to the invention are tablets or capsules, suspensions, solutions, gels, creams or ointments and aerosols in the form of sprays. The concentration used for solutions, gels, creams or ointments and aerosols in the form of sprays is generally between 0.1 and 3 percent by weight. Oral administration is carried out in customary pharmaceutical formulations, for example in the form of tablets or capsules which, per daily dose, contain 50–200 mg of the active compound mixed with a conventional vehicle and/or excipient. It is possible to use, for example, suspensions, solutions, gels, creams, ointments or suppositories for topical administration. Suspensions or solutions in a concentration for administration between 0.1 and 5 percent by weight are suitable for parenteral administration.

The examples illustrate the invention.

I. Examples of preparation process (a) as claimed in claim 2.

6-[(2RS,4SR)-2-(2,4-Dichlorophenyl)-2-(1H-imidazol-1-ylmethyl)-1,3-dioxolan-4-ylmethyloxy]-1,2,3,4-tetrahydroisoquinoline 0.55 g of sodium hydride (50% suspension in oil) is added to a solution of 1.50 g of 6-hydroxy-1,2,3,4-tetrahydroisoquinoline in 30 ml of dimethyl sulfoxide, and the mixture is stirred at 50° C. until evolution of hydrogen has finished. 4.07 g of (2RS,4SR)-2-(2,4-dichlorophenyl)-2-(1H-imidazol-1-ylmethyl)-1,3-dioxolan-4-ylmethyl methanesulfonate are added and the mixture is stirred at 80° C. for 5 hours. The solvent is removed under oil pump vacuum, the residue is taken up with a mixture of 50 ml of water and 50 ml of methylene chloride, and the organic phase is extracted twice more by shaking with water, dried and evaporated in a rotary evaporator. The residue is chromatographed on silica gel using methanol as the mobile phase. 2.45 g of colorless oil (53% of theory), which gradually crystallizes, are obtained. Melting point 143°–145° C.

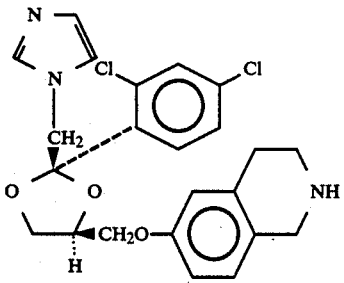

| Analysis: | Calculated: | Found: |
|---|---|---|
| $C_{23}H_{23}Cl_2N_3O_3$ | C 60.00 | C 59.4 |
| MW 460.36 | H 5.04 | H 5.2 |
| | N 9.13 | N 9.0 |

EXAMPLE 2

2-Allyl-6-[(2RS,4SR)-2-(2,4-dichlorophenyl)-2-(1H-imidazol-1-ylmethyl)-1,3-dioxolan-4-ylmethyloxy]-1,2,3,4-tetrahydroisoquinoline 1.89 g of 2-allyl-6-hydroxy-1,2,3,4-tetrahydroisoquinoline are added to a freshly prepared solution of alcoholate from 0.23 g of sodium in 30 ml of dry ethanol, the mixture is stirred for 15 minutes, 4.07 g of (2RS,4SR)-2-(2,4-dichlorophenyl)-2-(1H-imidazol-1-ylmethyl)-1,3-dioxolan-4-ylmethyl methanesulfonate are added, and the mixture is then heated under reflux for 8 hours. After cooling, the ethanol is removed in a rotary evaporator, and the residue is taken up with a mixture of 50 ml of water and 50 ml of methylene chloride. The organic phase is shaken twice more with water, dried over magnesium sulfate and evaporated in a rotary evaporator. The residue is purified by column chromatography on silica gel using a mixture of ethyl acetate/methanol 4:1. 1.3 g of a colorless resin (26% of theory) which gradually crystallizes is obtained. Melting point 94°–95° C.

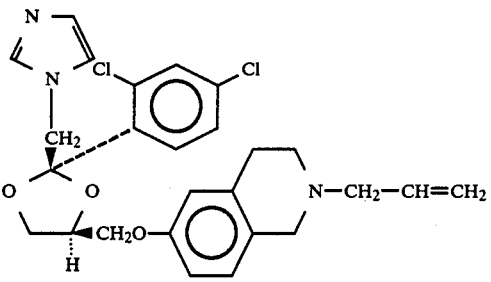

| Analysis: | Calculated: | Found: |
|---|---|---|
| $C_{26}H_{27}Cl_2N_3O_3$ | C 62.40 | 59.4 |
| MW 500.43 | H 5.44 | 5.5 |
| | N 8.40 | 8.3 |

EXAMPLE 3

6-[(2RS,4SR)-2-(2,4-Dichlorophenyl)-2-(1H-imidazol-1-ylmethyl)-1,3-dioxolan-4-ylmethyloxy]-2-(4-phenylbenzyl)-1,2,3,4-tetrahydroisoquinoline 0.26 g of sodium hydride (50% suspension in oil) is added to a solution of 0.75 g of 6-hydroxy-1,2,3,4-tetrahydroisoquinoline in 30 ml of dimethylformamide, and the mixture is stirred at 50° C. for 30 minutes. Then 2.04 g of (2RS,4SR)-2-(2,4-dichlorophenyl)-2-(1H-imidazol-1-ylmethyl)-1,3-dioxolan-4-ylmethyl methanesulfonate are introduced, and the mixture is stirred at 80° C. for 5 hours. It is allowed to cool, 1.00 g of finely powdered potassium carbonate and 1.00 g of 4-chloromethylbiphenyl are added, and the mixture is stirred at 60° C. for a further 5 hours. After cooling, the solvent is removed at the oil pump in a rotary evaporator, and the residue is taken up with a mixture of 50 ml of water and 50 ml of methylene chloride. The organic phase is washed twice more with water, dried over magnesium sulfate and evaporated in a rotary evaporator. To purify the crude product, it is chromatographed on silica gel using a mixture of ethyl acetate and methanol 19:1. 1.7 g of a viscous oil (57% of theory) which gradually crystallizes is obtained. Melting point 103°–105°.

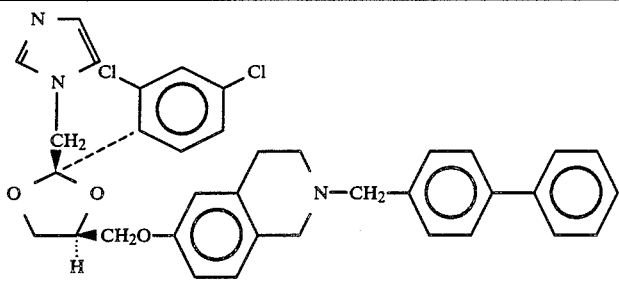

| Analysis: | Calculated: | Found: |
|---|---|---|
| C₃₆H₃₃Cl₂N₃O₃ | C 69.01 | C 68.8 |
| MW 626.59 | H 5.31 | H 5.4 |
|  | N 6.71 | N 6.8 |

EXAMPLE 4

6'-[(2RS,4SR)-2-(2,4-Dichlorophenyl)-2-(1H-imidazol-1-ylmethyl)-1,3-dioxolan-4-ylmethyloxy]-2'-methyl-1',2',3',4'-tetrahydrospiro[tetrahydrothiopyran-4,1'-isoquinoline]

0.26 g of sodium hydride (50% suspension in oil) is added to a solution of 1.19 g of 6'-hydroxy-1',2',3',4'-tetrahydrospiro[tetrahydrothiopyran-4,1'-isoquinoline]in 30 ml of dimethylformamide, and the mixture is stirred at 50° C. for 30 minutes. Then 2.04 g of (2RS,4SR)-2-(2,4-dichlorophenyl)-2-(1H-imidazol-1-ylmethyl)-1,3-dioxolan-4-ylmethyl methanesulfonate are introduced, and the mixture is stirred at 80° C. for 5 hours. After cooling, the mixture is washed with water, dried and evaporated in a rotary evaporator. The crude product is purified by chromatography on silica gel using a mixture of ethyl acetate/methanol 9:1. 2.0 g of pale yellow resin (71% of theory) which gradually crystallizes on standing are obtained. Melting point 138°-139°.

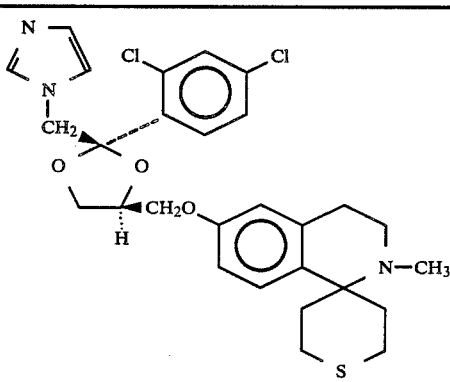

| Analysis: | Calculated: | Found: |
|---|---|---|
| C₂₈H₃₁Cl₂N₃O₃S | C 60.00 | C 59.5 |
| MW 560.55 | H 5.57 | H 5.5 |
|  | N 7.50 | N 7.5 |

EXAMPLE 5

6-[(2RS,4SR)-2-(2,4-Dichlorophenyl)-2-(1H-imidazol-1-ylmethyl)-1,3-dioxolan-4-ylmethyloxy]-2-(4-biphenylylacetyl)-1,2,3,4-tetrahydroisoquinoline A solution of 2.4 of 4-biphenylylacetyl chloride in 10 ml of methylene chloride is added dropwise, with stirring and cooling, to a solution of 4.6 g of the compound prepared according to Example 1 and 1.5 ml of triethylamine in 50 ml of methylene chloride. After extraction by shaking with water, 2N sodium hydroxide solution and again with water, the organic phase is dried over magnesium sulfate and evaporated in a rotary evaporator. The crude product is chromatographed on silica gel using a mixture of ethyl acetate/methanol 19:1. 3.2 g of a colorless resin (49% of theory) are obtained.

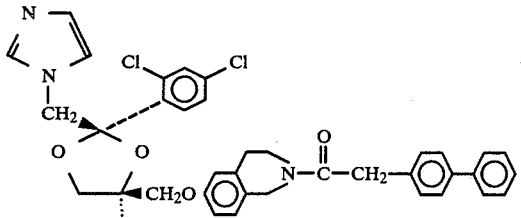

| Analysis: | Calculated: | Found: |
|---|---|---|
| C₃₇H₃₃Cl₂N₃O₄ | C 67.89 | C 67.7 |
| MW 654.60 | H 5.08 | H 5.0 |
|  | N 6.42 | N 6.4 |

EXAMPLE 6

6-[(2RS,4SR)-2-(2,4-Dichlorophenyl)-2-(1H-imidazol-1-ylmethyl)-1,3-dioxolan-4-ylmethyloxy]-2-(4-chloro-3-trifluoromethylbenzyl)-1,2,3,4-tetrahydroisoquinoline 0.3 g of sodium cyanoborohydride is added to a mixture of 1.75 g of the compound obtained according to Example 1, 0.80 g of 4-chloro-3-trifluoromethylbenzaldehyde and 0.7 g of toluenesulfonic acid monohydrate in 30 ml of ethanol, and the mixture is stirred at room temperature for 1 day. After removing the solvent in vacuo, the residue is taken up with a mixture of 2N sodium hydroxide solution and methylene chloride, the organic phase is washed with water, dried and evaporated in a rotary evaporator. The oily residue is chromatographed on silica gel using ethyl acetate. 1.0 g of a viscous resin (40% of theory) which crystallizes on trituration with diethyl ether is obtained. Melting point 107°-108°.

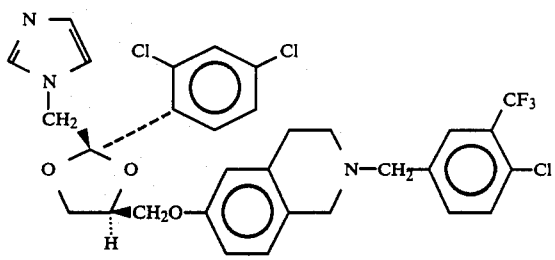

| Analysis: | Calculated: | Found: |
|---|---|---|
| $C_{31}H_{27}Cl_3F_3N_3O_3$ | C 57.03 | C 56.0 |
| MW: 652.93 | H 4.17 | H 4.3 |
| | N 6.44 | N 6.2 |

EXAMPLE 7

6-[(2RS,4SR)-2-(2,4-Dichlorophenyl)-2-(1H-imidazol-1-ylmethyl)-1,3-dioxolan-4-ylmethyloxy]-2-[2-(4-phenylbenzyl)ethyl]-1,2,3,4-tetrahydroisoquinoline A solution of 2.0 g of the compound prepared in accordance with Experiment 5 in 10 ml of dry tetrahydrofuran is added dropwise, with stirring, to a solution of 0.1 g of lithium aluminum hydride in 20 ml of dry tetrahydrofuran, and the mixture is stirred at 50° C. for 3 hours. Reagent is destroyed with water, inorganic material is removed by suction, the filtrate is dried over magnesium sulfate and the solvent is removed in vacuo. A viscous oil remains, and this is chromatographed on silica gel using a mixture of ethyl acetate/methanol 9:1. 1.0 g of a viscous oil (51% of theory) which gradually crystallizes on standing is obtained. Melting point 125°–127°.

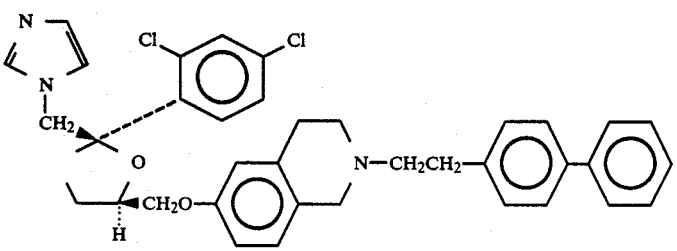

| Analysis | Calculated | Found |
|---|---|---|
| $C_{37}H_{35}Cl_2N_3O_3$ | C 69.37 | C 70.1 |
| MW: 640.61 | H 5.50 | H 5.6 |
| | N 6.56 | N 6.8 |

EXAMPLE 8

6-[(2RS,4SR)-2-(2,4-Dichlorophenyl)-2-(1H-imidazol-1-ylmethyl)-1,3-dioxolan-4-ylmethyloxy]-2-(4-fluorobenzyl)-1,2,3,4-tetrahydroisoquinoline A solution of 1.75 g of the compound prepared according to Example 1 is heated at 80° for 5 hours with 0.55 g of 4-fluorobenzyl chloride and 0.60 g of potassium carbonate in 30 ml of dimethylformamide. After cooling, the solvent is removed under oil pump vacuum, the residue is taken up with water/methylene chloride, and the organic phase is extracted twice by shaking with water, dried and evaporated in a rotary evaporator. The crude product is chromatographed on silica gel using a mixture of ethyl acetate/methanol 19:1. 1.5 g of a colorless oil (69% of theory) which crystallizes on standing are obtained. Melting point 119°–120°.

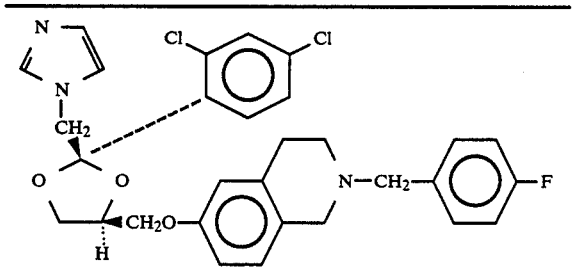

| Analysis | Calculated | Found |
|---|---|---|
| $C_{30}H_{28}Cl_2FN_3O_3$ | C 63.38 | C 62.8 |
| MW 568.48 | H 4.96 | H 5.0 |
| | N 7.39 | N 7.4 |

EXAMPLE 9

6-[(2RS,4SR)-2-(2,4-Dichlorophenyl)-2-(1H-imidazol-1-ylmethyl)-1,3-dioxolan-4-ylmethyloxy]-2-[2-(4-methoxyphenyl)ethyl]-1,2,3,4-tetrahydroisoquinoline 1.4 g of 6-hydroxy-2-[2-(4-methoxyphenyl)ethyl]-1,2,3,4-tetrahydroisoquinoline, 2.1 g of (2RS,4SR)-2-(2,4-dichlorophenyl)-2-(1H-imidazol-1-ylmethyl)-1,3-dioxolan-4-ylmethyl methanesulfonate and 0.3 g of tetrabutylammonium bromide are heated to reflux, with vigorous stirring, for 9 hours in a mixture of 40 ml of toluene and 10 ml of 50% strength sodium hydroxide solution. After cooling, 50 ml of water are added, and the organic phase is washed with water, dried over magnesium sulfate and evaporated in a rotary evaporator. The crude product is purified by column chromatography on silica gel using a mixture of ethyl acetate and methanol 19:1. 2.2 g of a colorless oil (76% of theory) which crystallizes on trituration with diethyl ether are obtained. Melting point: 121°–122°.

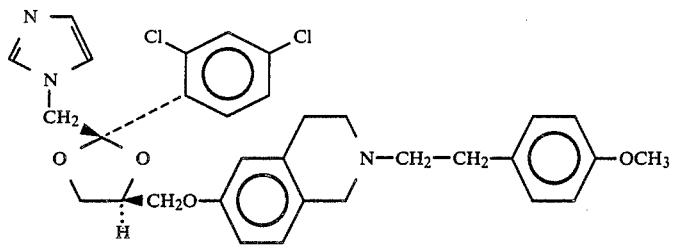

| Analysis | Calculated | Found |
|---|---|---|
| $C_{32}H_{33}Cl_3N_3O_4$ | C 64.65 | C 64.3 |
| MW: 594.54 | H 5.59 | H 5.5 |
| | N 7.07 | N 7.1 |

In addition, the compounds prepared below by process (b) are also obtained by process (a).

II. Examples of preparation process (b) as claimed in claim 2

EXAMPLE 10

(a)

6-[(2RS,4SR)-2-(4-chlorophenyl)-2-bromomethyl-1,3-dioxolan-4-ylmethyloxy]-2-(4-phenylbenzyl)-1,2,3,4-tetrahydroisoquinoline 1.1 g of sodium hydride (50% suspension in oil) are added in portions, with cooling, to a solution of 6.3 g of 6-hydroxy-2-(4-phenylbenzyl)-1,2,3,4-tetrahydroisoquinoline in 100 ml of dry dimethylformamide. The mixture is stirred at 50° for 1 hour and then 7.7 g of (2RS,4SR)-2-(4-chlorophenyl)-2-bromomethyl-1,3-dioxolan-4-ylmethyl methanesulfonate (preparation as in European Offenlegungsschrift No. 0,050,298) are added. The mixture is stirred at 80° C. for 5 hours and cooled, the solvent is removed under oil pump vacuum, and the residue is taken up with a mixture of water and methylene chloride. After washing twice with water and drying over magnesium sulfate, the solution is evaporated in a rotary evaporator, and the residue is chromatographed on silica gel with a mixture of methylene chloride and ethyl acetate in the ratio 3:1. 7.0 g of a highly viscous oil (58% of theory) are obtained.

(b)

6-[(2RS,4SR)-2-(4-chlorophenyl)-2-(1H-imidazol-1-ylmethyl)-1,3-dioxolan-4-ylmethyloxy]-2-(4-phenylbenzyl)-1,2,3,4-tetrahydroisoquinoline 1.5 g of imidazole are added, with stirring, to a suspension of 1.2 g of sodium hydride (50% suspension in oil) in 50 ml of dry dimethylacetamide, and the mixture is stirred until evolution of hydrogen is complete. Then a solution of 7.0 g of the bromomethyl derivative obtained under (a) in 10 ml of dimethylacetamide and a spatula tip of potassium iodide are added. The mixture is heated at 140° C. for 24 hours and cooled, and the solvent is removed under oil pump vacuum, and the residue is taken up with water/methylene chloride. After shaking twice with water, the organic phase is dried and evaporated in a rotary evaporator, and the residue is chromatographed on silica gel using a mixture of ethyl acetate and methanol in the ratio 19:1. 2.2 g of a highly viscous oil (32% of theory) are obtained.

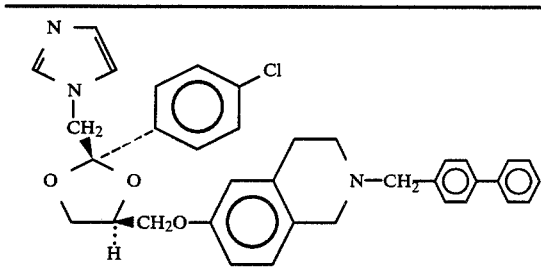

| Analysis | Calculated: | Found: |
|---|---|---|
| $C_{36}H_{34}ClN_3O_3$ | C 73.02 | C 72.3 |
| MW 592.14 | H 5.79 | H 5.7 |
| | N 7.10 | N 6.8 |

EXAMPLE 11

6-[(2RS,4SR)-2-(4-chlorophenyl)-2-(1H-imidazol-1-ylmethyl)-1,3-dioxolan-4-ylmethyloxy]-2-[3-(4-chlorophenyl)-propyl]-1,2,3,4-tetrahydroisoquinoline 550 mg of sodium hydride (50% suspension in oil) are added to a solution of 3.0 g of 6-hydroxy-2-[3-(4-chlorophenyl)propyl]-1,2,3,4-tetrahydroisoquinoline in 30 ml of dimethylacetamide, the mixture is stirred until evolution of hydrogen has ended, and 3.9 g of (2RS,4SR)-2-(4-chlorophenyl)-2-bromomethyl-1,3-dioxolan-4-ylmethyl methanesulfonate are added. The mixture is heated at 80° for 6 hours, and then 0.9 g of the sodium salt of imidazole and a spatula tip of potassium iodide are added. The solution is stirred at 100° for a further 6 hours. After cooling, the solvent is removed under oil pump vacuum, the residue is taken up with water/methylene chloride, and the organic phase is washed twice with water and dried over magnesium sulfate and the solvent is removed in vacuo. The crude product is purified by chromatography on silica gel using a mixture of ethyl acetate/methanol 9:1. 1.8 g of a viscous oil (31% of theory) which crystallizes on trituration with diethyl ether are obtained. Melting point: 101°–103°.

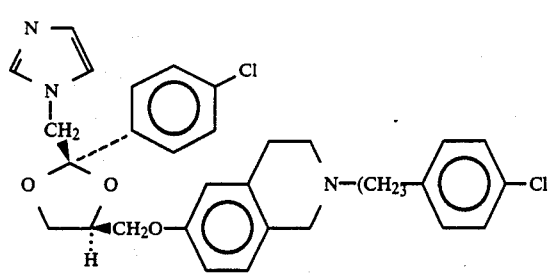

| Analysis | Calculated: | Found: |
|---|---|---|
| C₃₂H₃₃Cl₂N₃O₃ | C 66.43 | C 66.0 |
| MW 578.54 | H 5.75 | H 5.8 |
|  | N 7.26 | N 7.0 |

EXAMPLE 12

The following compounds of the general formula (I) listed in Table 1 can be prepared in analogy to Examples 1–11, but using equivalent amounts of the appropriate starting compounds.

TABLE 1

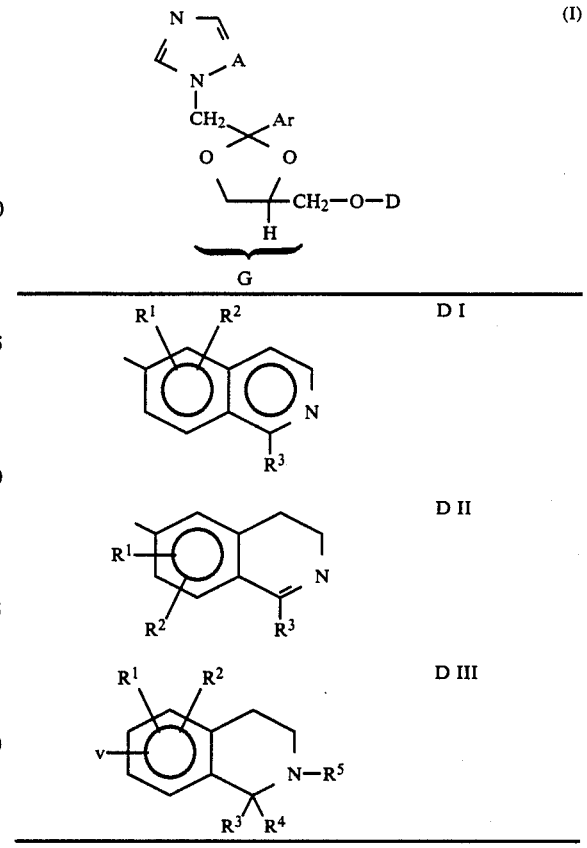

(a) in Table 1, v indicates the position of the G-CH₂O-radical on the isoquinoline radical D (b) cis and trans relate to the relative position of the azolylmethyl radical and the group —CH₂-O-D on the dioxolane ring.

| Compound No. | A | Ar | Isoquinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.1 | CH | 2,4-C₆H₃Cl₂ | DI | 6 | H | H | H | — | — | cis | 167 | 4 |
| 12.2 | CH | 2,4-C₆H₃Cl₂ | DI | 6 | H | H | —nC₇H₁₅ | — | — | cis | 108–109 | 4 |
| 12.3 | CH | 2,4-C₆H₃Cl₂ | DI | 6 | H | H | $\underset{CH_3}{\bigcirc}$ | — | — | cis | Resin | 4 |
| 12.4 | CH | 2,4-C₆H₃Cl₂ | DI | 6 | H | H | $\underset{Cl}{\bigcirc}$ | — | — | cis | Resin | 4 |
| 12.5 | CH | 2,4-C₆H₃Cl₂ | DII | 6 | H | H | —nC₇H₁₅ | — | — | cis | 86–88 | 4 |
| 12.6 | CH | 2,4-C₆H₃Cl₂ | DII | 6 | H | H | $\underset{Cl}{\bigcirc}$ | — | — | cis | Resin | 4 |
| 12.7 | CH | 2,4-C₆H₃Cl₂ | DII | 6 | 7-OCH₃ | H | $\underset{Cl}{\bigcirc}$ | — | — | cis | Resin | 4 |
| 12.8 | CH | 2,4-C₆H₃Cl₂ | DII | 6 | H | H | $\underset{Cl}{\bigcirc}$ | — | — | cis | 112 | 4 |
| 12.9 | CH | 2,4-C₆H₃Cl₂ | DIII | 6 | 7-OCH₃ | H | —(CH₂)₃—$\underset{Cl}{\bigcirc}$ | H | H | cis | Resin | 4 |
| 12.10 | CH | 2,4-C₆H₃Cl₃ | DIII | 6 | H | H | —C₂H₅ | H | CH₃ | cis | Resin | 4 |
| 12.11 | CH | 2,4-C₆H₃Cl₂ | DIII | 6 | H | H | CH₃ | CH₃ | CH₃ | cis | 110–112 | 4 |
| 12.12 | CH | 2,4-C₆H₃Cl₂ | DIII | 6 | H | H | —(CH₂)₅— | | CH₃ | cis | 127–130 | 4 |
| 12.13 | CH | 2,4-C₆H₃Cl₂ | DIII | 6 | H | H | —(CH₂)₂—O—(CH₂)₂— | | CH₃ | cis | Resin | 4 |
| 12.14 | CH | 2,4-C₆H₃Cl₂ | DIII | 6 | H | H | —(CH₂)₂—N(CH₃)—(CH₂)₂— | | CH₃ | cis | Resin | 4 |

-continued

| Compound No. | A | Ar | Iso-quinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.15 | CH | 2,4-C₆H₃Cl₂ | DIII | 6 | H | H | —(CH₂)₂—N—(CH₂)₂— <br>                      CH₂C₆H₅ | | CH₃ | cis | Resin | 4 |
| 12.16 | CH | 2,4-C₆H₃Cl₂ | DIII | 6 | H | H | —(CH₂)₂—N—(CH₂)₂— <br>                      COCH₃ | | CH₃ | cis | Resin | 4 |
| 12.17 | CH | 2,4-C₆H₃Cl₂ | DIII | 6 | H | H | —(CH₂)₂—N—(CH₂)₂— <br>                      COC₆H₅ | | CH₃ | cis | Resin | 4 |
| 12.18 | CH | 2,4-C₆H₃Cl₂ | DIII | 6 | H | H | —(CH₂)₂—N—(CH₂)₂— <br>                      COOC₂H₅ | | CH₃ | cis | Resin | 4 |
| 12.19 | CH | 2,4-C₆H₃Cl₂ | DIII | 6 | H | H | 4-Cl-C₆H₄ | H | CH₃ | cis | Resin | 4 |
| 12.20 | CH | 2,4-C₆H₃Cl₂ | DIII | 6 | H | H | 2,4-Cl₂-C₆H₃ | H | CH₃ | cis | Resin | 4 |
| 12.21 | CH | 2,4-C₆H₃Cl₂ | DIII | 6 | H | H | 4-CF₃-C₆H₄ | H | CH₃ | cis | Resin | 4 |
| 12.22 | CH | 2,4-C₆H₃Cl₂ | DIII | 6 | H | H | 4-OCH₃-C₆H₄ | H | CH₃ | cis | Resin | 4 |
| 12.23 | CH | 2,4-C₆H₃Cl₂ | DIII | 6 | H | H | 4-N(CH₃)₂-C₆H₄ | H | CH₃ | cis | Resin | 4 |

-continued

| Compound No. | A | Ar | Iso-quinoline type | V | $R_1$ | $R_2$ | $R_3$ | $R_4$ | $R_5$ | Isomerism at the dioxolane ring | Melting point [°C.] | Preparation in analogy to Example |
|---|---|---|---|---|---|---|---|---|---|---|---|---|
| 12.24 | CH | 2,4-$C_6H_3Cl_2$ | DIII | 6 | H | H |  | H | $CH_3$ | cis | 130–135 | 4 |
| 12.25 | CH | 2,4-$C_6H_3Cl_2$ | DIII | 6 | H | H |  | H | $CH_3$ | cis | Resin | 4 |
| 12.26 | CH | 2,4-$C_6H_3Cl_2$ | DIII | 6 | H | H | 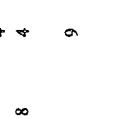 | H | $CH_3$ | cis | Resin | 4 |
| 12.27 | CH | 2,6-$C_6H_3Cl_2$ | DIII | 6 | H | H | H | H | $CH_3$ | cis | 120–121 | 4 |
| 12.28 | CH | 2,6-$C_6H_3Cl_2$ | DIII | 6 | 5$CH_3$ | 7$CH_3$ | H | H | $CH_3$ | cis | Resin | 4 |
| 12.29 | CH | 2,6-$C_6H_3Cl_2$ | DIII | 6 | H | H | H | H | $-nC_4H_9$ | cis | | 4 |
| 12.30 | CH | 2,4-$C_6H_3Cl_2$ | DIII | 6 | H | H | H | H | $-nC_8H_{17}$ | cis | 99–100 | 4 |
| 12.31 | CH | 2,4-$C_6H_3Cl_2$ | DIII | 6 | H | H | H | H | $-nC_{12}H_{25}$ | cis | 117–118 | 4 |
| 12.32 | CH | 2,4-$C_6H_3Cl_2$ | DIII | 6 | H | H | H | H | $-CH_2-C\equiv CH$ | cis | | 4 |
| 12.33 | CH | 2,4-$C_6H_3Cl_2$ | DIII | 6 | H | H | H | H |  | cis | 88 | 9 |
| 12.34 | CH | 2,4-$C_6H_3Cl_2$ | DIII | 7 | H | H | H | H |  | cis | | 9 |
| 12.35 | CH | 2,4-$C_6H_3Cl_2$ | DIII | 5 | H | H | H | H |  | cis | Resin | 4 |

-continued

| Compound No. | A | Ar | Iso-quinoline type | V | $R_1$ | $R_2$ | $R_3$ | $R_4$ | $R_5$ | Isomerism at the dioxolane ring | Melting point [°C.] | Preparation in analogy to Example |
|---|---|---|---|---|---|---|---|---|---|---|---|---|
| 12.36 | CH | 2,4-$C_6H_3Cl_2$ | DIII | 6 | H | H | H | H | $-CH_2-\phi-Cl$ (4-Cl) | cis | Resin | 4 |
| 12.37 | CH | 2,4-$C_6H_3Cl_2$ | DIII | 7 | H | H | H | H | $-CH_2-\phi-Cl$ (4-Cl) | cis | Resin | 4 |
| 12.38 | CH | biphenyl | DIII | 6 | H | H | H | H | $-CH_2-\phi-Cl$ (4-Cl) | cis | 168 | 4 |
| 12.39 | CH | 2,4-$C_6H_3Cl_2$ | DIII | 6 | H | H | H | H | $-CH_2-\phi-CF_3$ (4-$CF_3$) | cis | 125 | 9 |
| 12.40 | CH | 2,4-$C_6H_3Cl_2$ | DIII | 7 | H | H | H | H | $-CH_2-\phi-CF_3$ (4-$CF_3$) | cis | (Resin) | 9 |
| 12.41 | CH | 2,4-$C_6H_3Cl_2$ | DIII | 6 | H | H | H | H | $-CH_2-\phi(3,5-Cl_2)$ | cis |  | 4 |
| 12.42 | CH | 2,4-$C_6H_3Cl_2$ | DIII | 6 | H | H | H | H | $-CH_2-\phi(2,4-Cl_2)$ | cis | 144–145 | 4 |

-continued
| Compound No. | A | Ar | Iso-quinoline type | V | $R_1$ | $R_2$ | $R_3$ | $R_4$ | $R_5$ | Isomerism at the dioxolane ring | Melting point [°C.] | Preparation in analogy to Example |
|---|---|---|---|---|---|---|---|---|---|---|---|---|
| 12.43 | CH | 2,4-$C_6H_3Cl_2$ | DIII | 6 | H | H | H | H |  | cis | Resin | 4 |
| 12.44 | CH | 2,4-$C_6H_3Cl_2$ | DIII | 6 | H | H | H | H |  | cis | 114–115 | 4 |
| 12.45 | CH | 2,4-$C_6H_3Cl_2$ | DIII | 6 | H | H | H | H |  | cis | | 4 |
| 12.46 | CH | 2,4-$C_6H_3Cl_2$ | DIII | 7 | H | H | H | H |  | cis | | 4 |
| 12.47 | CH | 2,4-$C_6H_3Cl_2$ | DIII | 7 | H | H | H | H |  | cis | Resin | 9 |
| 12.48 | CH | 2,4-$C_6H_3Cl_2$ | DIII | 6 | H | H | H | H |  | cis | Resin | 9 |
| 12.49 | CH | 2,4-$C_6H_3Cl_2$ | DIII | 6 | H | H | H | H | —CH$_2$—C$_6$H$_4$—OCH$_3$ (p) | cis | 124–126 | 9 |

-continued

| Compound No. | A | Ar | Isoquinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.50 | CH | 2,4-C₆H₃Cl₂ | DIII | 7 | H | H | H | H | —CH₂—C₆H₄—OCH₃ | cis | | 9 |
| 12.51 | CH | 2,4-C₆H₃Cl₂ | DIII | 6 | H | H | H | H | —CH₂—C₆H₄—N(CH₃)₂ | cis | 91–92 | 9 |
| 12.52 | CH | 2,4-C₆H₃Cl₂ | DIII | 7 | H | H | H | H | —CH₂—C₆H₄—N(CH₃)₂ | cis | | 9 |
| 12.53 | CH | 2,4-C₆H₃Cl₂ | DIII | 6 | H | H | H | H | —CH₂—C₆H₄—SCH₃ | cis | 80–82 | 4 |
| 12.54 | CH | 2,4-C₆H₃Cl₂ | DIII | 7 | H | H | H | H | —CH₂—C₆H₄—SCH₃ | cis | Resin | 9 |
| 12.55 | CH | 2,4-C₆H₃Cl₂ | DIII | 6 | H | H | H | H | —CH₂—C₆H₄—S—C₆H₄—Cl | cis | Resin | 4 |
| 12.56 | CH | 2,4-C₆H₃Cl₂ | DIII | 6 | H | H | H | H | —CH₂—C₆H₄—O—C₆H₅ | cis | | 4 |
| 12.57 | CH | 2,4-C₆H₃Cl₂ | DIII | 7 | H | H | H | H | ″ | cis | | 4 |
| 12.58 | CH | 2,4-C₆H₃Cl₂ | DIII | 6 | H | H | H | H | —CH₂—C₆H₄—C₆H₅ | trans | Resin | 4 |

-continued

| Compound No. | A | Ar | Iso-quinoline type | V | $R_1$ | $R_2$ | $R_3$ | $R_4$ | $R_5$ | Isomerism at the dioxolane ring | Melting point [°C] | Preparation in analogy to Example |
|---|---|---|---|---|---|---|---|---|---|---|---|---|
| 12.59 | CH | 2,4-$C_6H_3Cl_2$ | DIII | 7 | H | H | H | H | —$CH_2$—(4-biphenyl) | cis | Resin | 4 |
| 12.60 | CH | 2,4-$C_6H_3Cl_2$ | DIII | 6 | 5-$CH_3$ | 7-$CH_3$ | H | H | —$CH_2$—(4-biphenyl) | cis | Resin | 4 |
| 12.61 | CH | 2,4-$C_6H_3Cl_2$ | DIII | 6 | 7-$OCH_3$ | H | H | H | —$CH_2$—(4-biphenyl) | cis | Resin | 4 |
| 12.62 | CH | 2,4-$C_6H_3Cl_2$ | DIII | 6 | H | H | H | H | —$CH_2$-(2-thienyl) | cis | Resin | 9 |
| 12.63 | CH | 2,4-$C_6H_3Cl_2$ | DIII | 7 | H | H | H | H | —$CH_2$-(2-thienyl) | cis | Resin | 9 |
| 12.64 | CH | 2,4-$C_6H_3Cl_2$ | DIII | 6 | H | H | H | H | —$CH_2$-(3-thienyl) | cis | Resin | 9 |
| 12.65 | CH | 2,4-$C_6H_3Cl_2$ | DIII | 7 | H | H | H | H | —$CH_2$-(3-thienyl) | cis | Resin | 9 |
| 12.66 | CH | 2,4-$C_6H_3Cl_2$ | DIII | 6 | H | H | H | H | —$CH_2$-(2-furyl) | cis | 99–101 | 4 |

-continued
| Compound No. | A | Ar | Iso-quinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.67 | CH | 2,4-C₆H₃Cl₂ | DIII | 7 | H | H | H | H |  | cis | | 4 |
| 12.68 | CH | 2,4-C₆H₃Cl₂ | DIII | 6 | H | H | H | H |  | cis | 116–118 | 4 |
| 12.69 | CH | 2,4-C₆H₃Cl₂ | DIII | 6 | H | H | H | H | 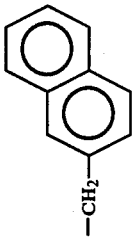 | cis | 150–152 | 4 |
| 12.70 | CH | 2,4-C₆H₃Cl₂ | DIII | 7 | H | H | H | H | 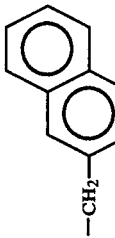 | cis | | 4 |
| 12.71 | CH | 2,4-C₆H₃Cl₂ | DIII | 6 | H | H | H | H | 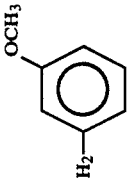 | cis | 96–98 | 4 |
| 12.72 | CH | 2,4-C₆H₃Cl₂ | DIII | 6 | H | H | H | H | 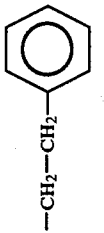 | cis | | 9 |
| 12.73 | CH | 2,4-C₆H₃Cl₂ | DIII | 7 | H | H | H | H | 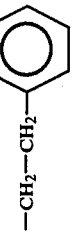 | cis | | 9 |

-continued

| Compound No. | A | Ar | Iso-quinoline type | V | R₁ | R₂ | R₃ | R₄ | R₅ | Isomerism at the dioxolane ring | Melting point [°C.] | Preparation in analogy to Example |
|---|---|---|---|---|---|---|---|---|---|---|---|---|
| 12.74 | CH | 2,4-C₆H₃Cl₂ | DIII | 6 | H | H | H | H | —CH₂—CH₂—C₆H₄—Cl | cis | 104–106 | 4 |
| 12.75 | CH | 2,4-C₆H₃Cl₂ | DIII | 6 | H | H | H | H | —CH₂—CH₂—C₆H₄—Cl | trans | 121–123 | 4 |
| 12.76 | CH | 4-biphenyl | DIII | 6 | H | H | H | H | —CH₂—CH₂—C₆H₄—Cl | cis | | 9 |
| 12.77 | CH | 2,4-C₆H₃Cl₂ | DIII | 7 | H | H | H | H | —CH₂—CH₂—C₆H₄—Cl | cis | 107–109 | 9 |
| 12.78 | CH | 2,4-C₆H₃Cl₂ | DIII | 7 | H | H | H | H | —CH₂—CH₂—C₆H₄—OCH₃ | cis | | 9 |
| 12.79 | CH | 2,4-C₆H₃Cl₂ | DIII | 6 | H | H | H | H | —CH₂—CH₂—C₆H₃(OCH₃)₂ | cis | | 9 |
| 12.80 | CH | 2,4-C₆H₃Cl₂ | DIII | 6 | H | H | H | H | —CH₂—CH₂—C₆H₄—CF₃ | cis | | 9 |

-continued

| Compound No. | A | Ar | Isoquinoline type | V | $R_1$ | $R_2$ | $R_3$ | $R_4$ | $R_5$ | Isomerism at the dioxolane ring | Melting point [°C] | Preparation in analogy to Example |
|---|---|---|---|---|---|---|---|---|---|---|---|---|
| 12.81 | CH | 2,4-$C_6H_3Cl_2$ | DIII | 6 | H | H | H | H | —$CH_2$—$CH_2$—(4-F-$C_6H_4$) | cis | | 9 |
| 12.82 | CH | 2,4-$C_6H_3Cl_2$ | DIII | 7 | H | H | H | H | —$CH_2$—$CH_2$—(4-F-$C_6H_4$) | cis | | 9 |
| 12.83 | CH | 2,4-$C_6H_3Cl_2$ | DIII | 7 | H | H | H | H | —$CH_2$—$CH_2$—(biphenyl) | cis | | 9 |
| 12.84 | CH | 2,4-$C_6H_3Cl_2$ | DIII | 6 | H | H | H | H | —$CH_2$—$CH_2$—(2-naphthyl) | cis | | 9 |
| 12.85 | CH | 2,4-$C_6H_3Cl_2$ | DIII | 6 | H | H | H | H | —$CH_2$—$CH_2$—(2-thienyl) | cis | | 9 |
| 12.86 | CH | 2,4-$C_6H_3Cl_2$ | DIII | 7 | H | H | H | H | —$CH_2$—$CH_2$—(2-thienyl) | cis | | 9 |
| 12.87 | CH | 2,4-$C_6H_3Cl_2$ | DIII | 6 | H | H | H | H | —$CH_2$—$CH_2$—(3-thienyl) | cis | | 4 |
| 12.88 | CH | 2,4-$C_6H_3Cl_2$ | DIII | 7 | H | H | H | H | —$CH_2$—$CH_2$—(3-thienyl) | cis | | 4 |

-continued

| Compound No. | A | Ar | Iso-quinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.89 | CH | 2,4-C₆H₃Cl₂ | DIII | 6 | H | H | H | H | —CH₂—CH₂—(3-pyridyl) | cis | | 4 |
| 12.90 | CH | 2,4-C₆H₃Cl₂ | DIII | 6 | H | H | H | H | —CH₂—CH₂—CH₂—C₆H₅ | cis | | 9 |
| 12.91 | CH | 2,4-C₆H₃Cl₂ | DIII | 7 | H | H | H | H | " | cis | | 9 |
| 12.92 | CH | 2,4-C₆H₃Cl₂ | DIII | 6 | H | H | H | H | —CH₂—CH₂—(4-Cl-C₆H₄) | cis | 112–114 | 4 |
| 12.93 | CH | 4-biphenylyl | DIII | 6 | H | H | H | H | —CH₂—CH₂—(4-Cl-C₆H₄) | cis | Resin | 4 |
| 12.94 | CH | 2,4-C₆H₃Cl₂ | DIII | 7 | H | H | H | H | —CH₂—CH₂—(4-Cl-C₆H₄) | cis | | 9 |
| 12.95 | CH | 2,4-C₆H₃Cl₂ | DIII | 6 | H | H | H | H | —CH₂—CH₂—CH₂—(4-F-C₆H₄) | cis | | 4 |
| 12.96 | CH | 2,4-C₆H₃Cl₂ | DIII | 7 | H | H | H | H | —CH₂—CH₂—CH₂—(4-F-C₆H₄) | cis | | 4 |
| 12.97 | CH | 2,4-C₆H₃Cl₂ | DIII | 6 | H | H | H | H | —CH₂—CH₂—CH₂—(4-CF₃-C₆H₄) | cis | 102–103 | 4 |

-continued

| Compound No. | A | Ar | Iso-quinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.98 | CH | 2,4-C₆H₃Cl₂ | DIII | 7 | H | H | H | H | —CH₂—CH₂—CH₂—C₆H₄—CF₃ | cis | | 4 |
| 12.99 | CH | 2,4-C₆H₃Cl₂ | DIII | 6 | H | H | H | H | —CH₂—CH₂—CH₂—C₆H₄—OCH₃ | cis | 110–111 | 4 |
| 12.100 | CH | 2,4-C₆H₃Cl₂ | DIII | 7 | H | H | H | H | —CH₂—CH₂—CH₂—C₆H₄—OCH₃ | cis | | 4 |
| 12.101 | CH | 2,4-C₆H₃Cl₂ | DIII | 6 | H | H | H | H | —CH₂—CH₂—CH₂-(2-thienyl) | cis | | 4 |
| 12.102 | CH | 2,4-C₆H₃Cl₂ | DIII | 7 | H | H | H | H | —CH₂—CH₂—CH₂-(2-thienyl) | cis | | 4 |
| 12.103 | CH | 2,4-C₆H₃Cl₂ | DIII | 6 | H | H | H | H | —CH₂—CH₂—CH₂-(3-thienyl) | cis | | 4 |
| 12.104 | CH | 2,4-C₆H₃Cl₂ | DIII | 7 | H | H | H | H | —CH₂—CH₂—CH₂-(3-thienyl) | cis | | 4 |
| 12.105 | CH | 2,4-C₆H₃Cl₂ | DIII | 6 | H | H | H | H | —CH₂—CH₂—CH₂-(4-pyridyl) | cis | | 4 |

-continued

| Compound No. | A | Ar | Isoquinoline type | V | R₁ | R₂ | R₃ | R₄ | R₅ | Isomerism at the dioxolane ring | Melting point [°C.] | Preparation in analogy to Example |
|---|---|---|---|---|---|---|---|---|---|---|---|---|
| 12.106 | CH | 2,4-C₆H₃Cl₂ | DIII | 6 | H | H | H | H | —(CH₂)₄—C₆H₅ | cis | | 9 |
| 12.107 | CH | 2,4-C₆H₃Cl₂ | DIII | 7 | H | H | H | H | —(CH₂)₄—C₆H₅ | cis | | 9 |
| 12.108 | CH | 2,4-C₆H₃Cl₂ | DIII | 6 | H | H | H | H | —(CH₂)₄—C₆H₄-4-Cl | cis | 101–103 | 4 |
| 12.109 | CH | 2,4-C₆H₃Cl₂ | DIII | 7 | H | H | H | H | —(CH₂)₄—C₆H₄-4-Cl | cis | | 4 |
| 12.110 | CH | 2,4-C₆H₃Cl₂ | DIII | 6 | H | H | H | H | —(CH₂)₄—C₆H₄-4-OCH₃ | cis | | 4 |
| 12.111 | CH | 2,4-C₆H₃Cl₂ | DIII | 7 | H | H | H | H | —(CH₂)₄—C₆H₄-4-OCH₃ | cis | | 4 |
| 12.112 | CH | 2,4-C₆H₃Cl₂ | DIII | 6 | H | H | H | H | —(CH₂)₄—C₆H₄-4-F | cis | | 4 |
| 12.113 | CH | 2,4-C₆H₃Cl₂ | DIII | 7 | H | H | H | H | —(CH₂)₄—C₆H₄-4-F | cis | | 4 |

-continued

| Compound No. | A | Ar | Iso-quino-line type | V | $R_1$ | $R_2$ | $R_3$ | $R_4$ | $R_5$ | Isomerism at the dioxolane ring | Melting point [°C] | Preparation in analogy to Example |
|---|---|---|---|---|---|---|---|---|---|---|---|---|
| 12.114 | CH | 2,4-$C_6H_3Cl_2$ | DIII | 6 | H | H | H | H | —$(CH_2)_4$—C$_6$H$_4$—C$_6$H$_5$ | cis | | 4 |
| 12.115 | CH | 2,4-$C_6H_3Cl_2$ | DIII | 7 | H | H | H | H | —$(CH_2)_4$—C$_6$H$_4$—C$_6$H$_5$ | cis | | 4 |
| 12.116 | CH | 2,4-$C_6H_3Cl_2$ | DIII | 6 | H | H | H | H | —$(CH_2)_4$-thienyl | cis | | 4 |
| 12.117 | CH | 2,4-$C_6H_3Cl_2$ | DIII | 7 | H | H | H | H | —$(CH_2)_4$-thienyl | cis | | 4 |
| 12.118 | CH | 2,4-$C_6H_3Cl_2$ | DIII | 6 | H | H | H | H | —$(CH_2)_5$—C$_6$H$_5$ | cis | | 4 |
| 12.119 | CH | 2,4-$C_6H_3Cl_2$ | DIII | 7 | H | H | H | H | —$(CH_2)_5$—C$_6$H$_5$ | cis | | 4 |
| 12.120 | CH | 2,4-$C_6H_3Cl_2$ | DIII | 6 | H | H | H | H | —$(CH_2)_5$—C$_6$H$_4$—Cl | cis | | 4 |
| 12.121 | CH | 2,4-$C_6H_3Cl_2$ | DIII | 7 | H | H | H | H | —$(CH_2)_5$—C$_6$H$_4$—Cl | cis | | 4 |
| 12.122 | CH | 2,4-$C_6H_3Cl_2$ | DIII | 6 | H | H | H | H | —$(CH_2)_5$—C$_6$H$_4$—OCH$_3$ | cis | | 4 |

-continued

| Compound No. | A | Ar | Iso-quino-line type | V | $R_1$ | $R_2$ | $R_3$ | $R_4$ | $R_5$ | Isomerism at the dioxolane ring | Melting point [°C] | Preparation in analogy to Example |
|---|---|---|---|---|---|---|---|---|---|---|---|---|
| 12.123 | CH | 2,4-$C_6H_3Cl_2$ | DIII | 7 | H | H | H | H | —$(CH_2)_5$—C$_6$H$_4$—OCH$_3$ | cis | | 4 |
| 12.124 | CH | 2,4-$C_6H_3Cl_2$ | DIII | 6 | H | H | H | H | —$(CH_2)_5$—C$_6$H$_4$—F | cis | | 4 |
| 12.125 | CH | 2,4-$C_6H_3Cl_2$ | DIII | 7 | H | H | H | H | —$(CH_2)_5$—C$_6$H$_4$—F | cis | | 4 |
| 12.126 | CH | 2,4-$C_6H_3Cl_2$ | DIII | 6 | H | H | H | H | —$(CH_2)_5$—C$_6$H$_4$—C$_6$H$_5$ | cis | | 4 |
| 12.127 | CH | 2,4-$C_6H_3Cl_2$ | DIII | 7 | H | H | H | H | —$(CH_2)_5$—C$_6$H$_4$—C$_6$H$_5$ | cis | | 4 |
| 12.128 | CH | 2,4-$C_6H_3Cl_2$ | DIII | 6 | H | H | H | H | —$(CH_2)_5$-thienyl | cis | | 4 |
| 12.129 | CH | 2,4-$C_6H_3Cl_2$ | DIII | 7 | H | H | H | H | —$(CH_2)_5$-thienyl | cis | | 4 |
| 12.130 | CH | 2,4-$C_6H_3Cl_2$ | DIII | 7 | H | H | H | H | H | cis | Resin | 1 |
| 12.131 | CH | 2,4-$C_6H_3Cl_2$ | DIII | 6 | H | H | H | H | —COCH$_3$ | cis | | 4 |
| 12.132 | CH | 2,4-$C_6H_3Cl_2$ | DIII | 7 | H | H | H | H | —COCH$_3$ | cis | | 4 |

-continued
| Compound No. | A | Ar | Isoquinoline type | V | $R_1$ | $R_2$ | $R_3$ | $R_4$ | $R_5$ | Isomerism at the dioxolane ring | Melting point [°C] | Preparation in analogy to Example |
|---|---|---|---|---|---|---|---|---|---|---|---|---|
| 12.133 | CH | 2,4-$C_6H_3Cl_2$ | DIII | 6 | H | H | H | H | 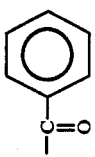 | cis | | 4 |
| 12.134 | CH | 2,4-$C_6H_3Cl_2$ | DIII | 7 | H | H | H | H |  | cis | | 4 |
| 12.135 | CH | 2,4-$C_6H_3Cl_2$ | DIII | 6 | H | H | H | H | 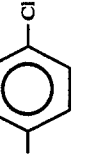 | cis | Resin | 4 |
| 12.136 | CH | 2,4-$C_6H_3Cl_2$ | DIII | 7 | H | H | H | H | 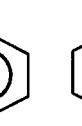 | cis | | 4 |
| 12.137 | CH | 2,4-$C_6H_3Cl_2$ | DIII | 6 | H | H | H | H | 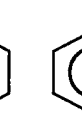 | cis | | 4 |
| 12.138 | CH | 2,4-$C_6H_3Cl_2$ | DIII | 7 | H | H | H | H | 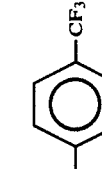 | cis | | 4 |
| 12.139 | CH | 2,4-$C_6H_3Cl_2$ | DIII | 6 | H | H | H | H | 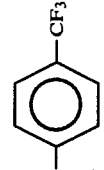 | cis | | 4 |
| 12.140 | CH | 2,4-$C_6H_3Cl_2$ | DIII | 7 | H | H | H | H |  | cis | | 4 |

-continued

| Compound No. | A | Ar | Isoquinoline type | v | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.141 | CH | 2,4-C₆H₃Cl₂ | DIII | 6 | H | H | H | H | –C(=O)–C₆H₄–OCH₃ (4-OCH₃) | cis | Resin | 4 |
| 12.142 | CH | 2,4-C₆H₃Cl₂ | DIII | 7 | H | H | H | H | –C(=O)–C₆H₄–OCH₃ (4-OCH₃) | cis | | 4 |
| 12.143 | CH | 2,4-C₆H₃Cl₂ | DIII | 6 | H | H | H | H | –C(=O)–C₆H₃(OCH₃)₂ (3,4-diOCH₃) | cis | | 4 |
| 12.144 | CH | 2,4-C₆H₃Cl₂ | DIII | 7 | H | H | H | H | –C(=O)–C₆H₃(OCH₃)₂ (3,4-diOCH₃) | cis | | 4 |
| 12.145 | CH | 2,4-C₆H₃Cl₂ | DIII | 6 | H | H | H | H | –C(=O)–C₆H₂(OCH₃)₃ (3,4,5-triOCH₃) | cis | | 4 |
| 12.146 | CH | 2,4-C₆H₃Cl₂ | DIII | 7 | H | H | H | H | –C(=O)–C₆H₂(OCH₃)₃ (3,4,5-triOCH₃) | cis | | 4 |
| 12.147 | CH | 2,4-C₆H₃Cl₂ | DIII | 6 | H | H | H | H | –C(=O)–C₆H₄–N(CH₃)₂ | cis | Resin | 4 |

-continued
| Compound No. | A | Ar | Iso-quinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.148 | CH | 2,4-C₆H₃Cl₂ | DIII | 7 | H | H | H | H | 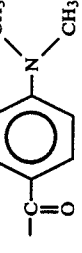 | cis | | 4 |
| 12.149 | CH | 2,4-C₆H₃Cl₂ | DIII | 6 | H | H | H | H | 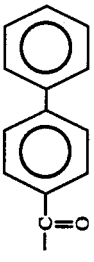 | cis | | 4 |
| 12.150 | CH | 2,4-C₆H₃Cl₂ | DIII | 7 | H | H | H | H | 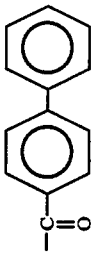 | cis | | 4 |
| 12.151 | CH | 2,4-C₆H₃Cl₂ | DIII | 6 | H | H | H | H | 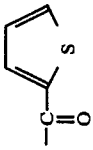 | cis | | 4 |
| 12.152 | CH | 2,4-C₆H₃Cl₂ | DIII | 7 | H | H | H | H | 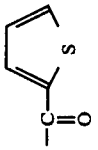 | cis | | 4 |
| 12.153 | CH | 2,4-C₆H₃Cl₂ | DIII | 6 | H | H | H | H | 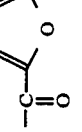 | cis | | 4 |
| 12.154 | CH | 2,4-C₆H₃Cl₂ | DIII | 7 | H | H | H | H | 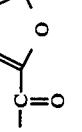 | cis | | 4 |
| 12.155 | CH | 2,4-C₆H₃Cl₂ | DIII | 6 | H | H | H | H | 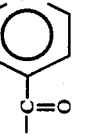 | cis | | 4 |

-continued

| Compound No. | A | Ar | Isoquinoline type | V | R₁ | R₂ | R₃ | R₄ | R₅ | Isomerism at the dioxolane ring | Melting point [°C.] | Preparation in analogy to Example |
|---|---|---|---|---|---|---|---|---|---|---|---|---|
| 12.156 | CH | 2,4-C₆H₃Cl₂ | DIII | 7 | H | H | H | H | 4-pyridyl-C(=O)- | cis | | 4 |
| 12.157 | CH | 2,4-C₆H₃Cl₂ | DIII | 6 | H | H | H | H | 3-pyridyl-C(=O)- | cis | | 4 |
| 12.158 | CH | 2,4-C₆H₃Cl₂ | DIII | 7 | H | H | H | H | 3-pyridyl-C(=O)- | cis | | 4 |
| 12.159 | CH | 2,4-C₆H₃Cl₂ | DIII | 6 | H | H | H | H | 4-F-C₆H₄- | cis | | 9 |
| 12.160 | CH | 2,4-C₆H₃Cl₂ | DIII | 6 | H | H | H | H | 4-Cl-C₆H₄- | cis | 117–119 | 9 |
| 12.161 | CH | 2,4-C₆H₃Cl₂ | DIII | 6 | H | H | H | H | 4-Br-C₆H₄- | cis | | 9 |
| 12.162 | CH | 2,4-C₆H₃Cl₂ | DIII | 6 | H | H | H | H | 4-CH₃-C₆H₄- | cis | | 9 |
| 12.163 | CH | 2,4-C₆H₃Cl₂ | DIII | 6 | H | H | H | H | 4-CF₃-C₆H₄- | cis | | 9 |

-continued

| Compound No. | A | Ar | Iso-quinoline type | V | $R_1$ | $R_2$ | $R_3$ | $R_4$ | $R_5$ | Isomerism at the dioxolane ring | Melting point [°C] | Preparation in analogy to Example |
|---|---|---|---|---|---|---|---|---|---|---|---|---|
| 12.164 | CH | 2,4-$C_6H_3Cl_2$ | DIII | 6 | H | H | H | H | 3,5-dichlorophenyl | cis | | 9 |
| 12.165 | CH | 2,4-$C_6H_3Cl_2$ | DIII | 6 | H | H | H | H | 2,4-dichlorophenyl | cis | | 9 |
| 12.166 | CH | 2,4-$C_6H_3Cl_2$ | DIII | 6 | H | H | H | H | 4-(N,N-dimethylamino)phenyl | cis | | 9 |
| 12.167 | CH | 2,4-$C_6H_3Cl_2$ | DIII | 6 | H | H | H | H | 4-biphenylyl | cis | | 9 |
| 12.168 | CH | 2,4-$C_6H_3Cl_2$ | DIII | 6 | H | H | H | H | phenyl | cis | | 9 |
| 12.169 | CH | 2,4-$C_6H_3Cl_2$ | DIII | 6 | H | H | H | H | -$CH_2$-(2,4-dimethoxyphenyl) | cis | | 9 |
| 12.170 | CH | 2,4-$C_6H_3Cl_2$ | DIII | 7 | H | H | H | H | -$CH_2$-(2,4-dimethoxyphenyl) | cis | | 9 |

-continued

| Compound No. | A | Ar | Iso-quinoline type | V | R₁ | R₂ | R₃ | R₄ | R₅ | Isomerism at the dioxolane ring | Melting point [°C] | Preparation in analogy to Example |
|---|---|---|---|---|---|---|---|---|---|---|---|---|
| 12.171 | CH | 2,4-C₆H₃Cl₂ | DIII | 6 | H | H | H | H | −CH₂−C₆H₂(OCH₃)₃ (3,4,5-trimethoxybenzyl) | cis | 131 | 9 |
| 12.172 | CH | 2,4-C₆H₃Cl₂ | DIII | 7 | H | H | H | H | −CH₂−C₆H₂(OCH₃)₃ (3,4,5-trimethoxybenzyl) | cis | | 9 |
| 12.173 | CH | 2,4-C₆H₃Cl₂ | DIII | 6 | H | H | H | H | −CH₂−CH₂−C₆H₄−CF₃ | cis | 115–116 | 9 |
| 12.174 | CH | 2,4-C₆H₃Cl₂ | DIII | 7 | H | H | H | H | −CH₂−CH₂−C₆H₄−CF₃ | cis | | 9 |
| 12.175 | CH | 2,4-C₆H₃Cl₂ | DIII | 6 | H | H | H | H | −CH₂−C₆H₄−NO₂ (4-NO₂) | cis | | 9 |
| 12.176 | CH | 2,4-C₆H₃Cl₂ | DIII | 7 | H | H | H | H | −CH₂−C₆H₄−NO₂ (4-NO₂) | cis | | 9 |
| 12.177 | CH | 2,4-C₆H₃Cl₂ | DIII | 6 | H | H | H | H | −CH₂−C₆H₄−NO₂ (3-NO₂) | cis | | 9 |

-continued

| Compound No. | A | Ar | Iso-quinoline type | v | $R_1$ | $R_2$ | $R_3$ | $R_4$ | $R_5$ | Isomerism at the dioxolane ring | Melting point [°C.] | Preparation in analogy to Example |
|---|---|---|---|---|---|---|---|---|---|---|---|---|
| 12.178 | CH | 2,4-$C_6H_3Cl_2$ | DIII | 7 | H | H | H | H | —$CH_2$—C$_6$H$_4$-3-$NO_2$ | cis | | 9 |
| 12.179 | CH | 2,4-$C_6H_3Cl_2$ | DIII | 6 | H | H | H | H | —$CH_2$—$CH_2$—C$_6$H$_4$-4-$NO_2$ | cis | | 9 |
| 12.180 | CH | 2,4-$C_6H_3Cl_2$ | DIII | 7 | H | H | H | H | —$CH_2$—$CH_2$—C$_6$H$_4$-4-$NO_2$ | cis | | 9 |
| 12.181 | CH | 2,4-$C_6H_3Cl_2$ | DIII | 6 | H | H | H | H | —$CH_2$—$CH_2$—C$_6$H$_4$-3-$NO_2$ | cis | | 9 |
| 12.182 | CH | 2,4-$C_6H_3Cl_2$ | DIII | 7 | H | H | H | H | —$CH_2$—$CH_2$—C$_6$H$_4$-3-$NO_2$ | cis | | 9 |
| 12.183 | CH | 2,4-$C_6H_3Cl_2$ | DIII | 6 | H | H | H | H | —$(CH_2)_3$—C$_6$H$_4$-4-$NO_2$ | cis | | 9 |
| 12.184 | CH | 2,5-$C_6H_3Cl_2$ | DIII | 7 | H | H | H | H | —$(CH_2)_3$—C$_6$H$_4$-4-$NO_2$ | cis | | 9 |

| Compound No. | A | Ar | Iso-quinoline type | V | R₁ | R₂ | R₃ | R₄ | R₅ | Isomerism at the dioxolane ring | Melting point [°C.] | Preparation in analogy to Example |
|---|---|---|---|---|---|---|---|---|---|---|---|---|
| 12.185 | CH | 2,4-C₆H₃Cl₂ | DIII | 6 | H | H | H | H | —(CH₂)₃—C₆H₄(NO₂) | cis | | 9 |
| 12.186 | CH | 2,4-C₆H₃Cl₂ | DIII | 7 | H | H | H | H | —(CH₂)₃—C₆H₄(NO₂) | cis | | 9 |
| 12.187 | CH | 2,4-C₆H₃Cl₂ | DIII | 7 | H | H | H | H | —CH₂—C₆H₃Cl₂ (3,5) | cis | | 9 |
| 12.188 | CH | 2,4-C₆H₃Cl₂ | DIII | 7 | H | H | H | H | —CH₂—C₆H₃Cl₂ (3,4) | cis | | 9 |
| 12.189 | CH | 2,4-C₆H₃Cl₂ | DIII | 7 | H | H | H | H | —CH₂—C₆H₄(OCH₃) | cis | | 9 |
| 12.190 | CH | 2,4-C₆H₃Cl₂ | DIII | 7 | H | H | H | H | —CH₂—C₆H₃(Cl)(CF₃) | cis | | 9 |

-continued

| Compound No. | A | Ar | Iso-quinoline type | V | $R_1$ | $R_2$ | $R_3$ | $R_4$ | $R_5$ | Isomerism at the dioxolane ring | Melting point [°C.] | Preparation in analogy to Example |
|---|---|---|---|---|---|---|---|---|---|---|---|---|
| 12.191 | CH | 2,4-$C_6H_3Cl_2$ | DIII | 7 | H | H | H | H | —(CH$_2$)$_3$—  | cis | | 9 |
| 12.192 | CH | 2,4-$C_6H_3Cl_2$ | DIII | 6 | H | H | H | H | —CO— 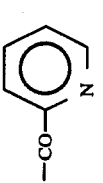 | cis | | 9 |
| 12.193 | CH | 2,4-$C_6H_3Cl_2$ | DIII | 7 | H | H | H | H | —CO— 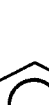 | cis | | 9 |
| 12.194 | CH | 2,4-$C_6H_3Cl_2$ | DIII | 7 | H | H | H | H | 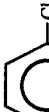 | cis | 93–95 | 9 |
| 12.195 | N | 2,4-$C_6H_3Cl_2$ | DIII | 6 | H | H | H | H | —CH$_2$— 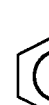 | cis | 105–107° | 9 |
| 12.196 | N | 2,4-$C_6H_3Cl_2$ | DIII | 6 | H | H | H | H | —(CH$_2$)$_2$— 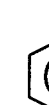 | cis | 98–100 | 9 |
| 12.197 | N | 2,4-$C_6H_3Cl_2$ | DIII | 6 | H | H | H | H | —(CH$_2$)$_3$— 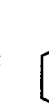 | cis | 91–93 | 9 |
| 12.198 | N | 2,4-$C_6H_3Cl_2$ | DIII | 6 | H | H | H | H | —(CH$_2$)$_4$— 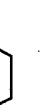 | cis | 93–95 | 9 |

-continued
| Compound No. | A | Ar | Iso-quino-line type | V | R₁ | R₂ | R₃ | R₄ | R₅ | Isomerism at the dioxolane ring | Melting point [°C.] | Preparation in analogy to Example |
|---|---|---|---|---|---|---|---|---|---|---|---|---|
| 12.199 | N | 2,4-C₆H₃Cl₂ | DIII | 6 | H | H | H | H |  —CH₂—C₆H₄—CF₃ | cis | 110–112 | 9 |
| 12.200 | N | 2,4-C₆H₃Cl₂ | DIII | 6 | H | H | H | H |  —(CH₂)₂—C₆H₄—CF₃ | cis | 105–107 | 9 |

III. For the preparation of compounds of the general formula (III).

EXAMPLE 13

6-Hydroxy-2-(4-chlorobenzoyl)-1,2,3,4-tetrahydroisoquinoline

Starting material for the preparation of compound 12.135 in Table 1

1.2 g of 6-hydroxy-1,2,3,4-tetrahydroisoquinoline are suspended in 50 ml of methylene chloride, 1.2 ml of triethylamine are added, and a solution of 1.4 g of 4-chlorobenzoyl chloride in 10 ml of methylene chloride is added dropwise with stirring and cooling. After standing overnight, the mixture is extracted by shaking with 2N hydrochloric acid and water, and the organic phase is dried and evaporated in a rotary evaporator. A colorless oil remains, and this crystallizes on trituration with ethyl acetate.

Yield: 1.8 g (78% of theory), melting point: 170°.

EXAMPLE 14

6-Hydroxy-2-(3-methoxybenzyl)-1,2,3,4-tetrahydroisoquinoline

Starting material for the preparation of compound 12.71 in Table 1

4.3 g of 6-hydroxy-1,2,3,4-tetrahydroisoquinoline hydrobromide, 3.1 g of 3-methoxybenzyl chloride and 2.8 g of finely powdered potassium carbonate are first stirred at room temperature for 2 hours and then at 80° C. for 5 hours. After cooling, the solvent is removed in vacuo, the residue is taken up with water/methylene chloride, and the organic phase is again shaken with water and dried over magnesium sulfate. After evaporation in a rotary evaporator, a yellow oil remains, and this crystallizes after trituration with ethyl acetate.

Yield: 2.6 g (52% of theory), melting point: 132°–134° C.

EXAMPLE 15

6-Hydroxy-2-(2-thienylmethyl)-1,2,3,4-tetrahydroisoquinoline

Starting material for the preparation of compound 12.62 in Table 1

0.6 g of sodium cyanoborohydride is added to a solution of 1.5 g of 6-hydroxy-1,2,3,4-tetrahydroisoquinoline, 1.2 g of thiophene-2-aldehyde and 1.8 g of toluenesulfonic acid monohydrate in 30 ml of ethanol. The mixture is stirred at room temperature for 8 hours, the solvent is removed in vacuo, and the residue is taken up with water/methylene chloride. The organic phase is again skaken with water, dried and evaporated in a rotary evaporator. The crude oily product is purified by chromatography on silica gel using a mixture of ethyl acetate/methylene chloride in the ratio 1:2. 1.7 g of a colorless oil, which crystallizes on standing (69% of theory), is obtained. Melting point: 110°–112° C.

EXAMPLE 16

6-Hydroxy-2-(4-phenylbenzyl)-1,2,3,4-tetrahydroisoquinoline

Starting material for the preparation of compound 12.58 in Table 1

(a) 6-Methoxy-2-(4-phenylbenzyl)-1,2,3,4-tetrahydroisoquinoline 4.0 g of 6-methoxy-1,2,3,4-tetrahydroisoquinoline hydrochloride, 4.1 g of 4-chloromethylbiphenyl and 6.0 g of finely powdered potassium carbonate in 50 ml of dimethylformamide are stirred at 80° for 5 hours. The solvent is removed in vacuo, the residue is taken up in water/methylene chloride, the organic phase is shaken twice with water, and the organic phase is dried with magnesium sulfate and evaporated in a rotary evaporator. The crude product, which is only slightly impure, can be reacted further without further purification. A sample recrystallized from ethyl acetate has a melting point of 120°.

(b) 6-Hydroxy-2-(4-phenylbenzyl)-1,2,3,4-tetrahydroisoquinoline

The above methoxy compound is heated under reflux for 6 hours with a mixture of 50 ml of glacial acetic acid and 48% strength aqueous hydrobromic acid in the volume ratio 1:1. After cooling, the acid mixture is distilled off under waterpump vacuum, and the solid residue is powdered, stirred with aqueous ammonia solution, filtered off with suction and washed with water. The crude product is boiled with ethanol and, after cooling, the solid is filtered off with suction. 5.0 g of colorless solid of melting point 235°–237° (79% of theory) are obtained.

EXAMPLE 17

6-Hydroxy-2-n-octyl-1,2,3,4-tetrahydroisoquinoline hydrobromide

Starting material for the preparation of compound No. 12.30 in Table 1

(a) 6-Methoxy-2-capryloyl-1,2,3,4-tetrahydroisoquinoline 4.0 g of 6-methoxy-1,2,3,4-tetrahydroisoquinoline and 3.5 ml of triethylamine in 50 ml of methylene chloride are initially introduced, and a solution of 4.0 g of octanoyl chloride in 10 ml of methylene chloride is added dropwise with stirring and cooling. The mixture is stirred at room temperature for 1 hour, then shaken with 1N hydrochloric acid, sodium carbonate solution and water, and the organic phase is dried over magnesium sulfate and evaporated in a rotary evaporator. The crude product (6.7 g of colorless oil) is reacted further without purification.

(b) 6-Methoxy-2-n-octyl-1,2,3,4-tetrahydroisoquinoline

The amide prepared under (a) is dissolved in 50 ml of dry diethyl ether and added dropwise to a suspension of 1.0 g of lithium aluminum hydride in 100 ml of dry diethyl ether. The mixture is then heated under reflux for 3 hours, 5 ml of water is added cautiously to cause decomposition, with cooling, and inorganic material is filtered off. The oil remaining after removal of the solvent in vacuo is reac-ted further without purification.

(c) 6-Hydroxy-2-n-octyl-1,2,3,4-tetrahydroisoquinoline hydrobromide 5.8 g of the compound prepared under (b) are heated under reflux for 16 hours with a mixture of 100 ml of glacial acetic acid and 48% strength aqueous hydrobromic acid in the volume ratio 1:1. After cooling, the acid mixture is distilled off under waterpump vacuum, and the residue is boiled with a little ethanol. On cooling and scratching, 4.0 g of colorless crystals crystallize out (47% of theory over all stages), melting point: 165–166°.

EXAMPLE 18

6'-Hydroxy-1',2',3',4'-tetrahydrospiro[tetrahydrothiopyran-4,1'-isoquinoline]

Starting material for Example 4

2.0 g of 6-hydroxy-N-methyl-β-phenethylamine and 1.6 g of tetrahydrothiopyran-4-one in 30 ml of ethanol are heated under reflux for 8 hours. On cooling the mixture, 1.4 g of colorless product crystallizes out (45% of theory), melting point 211°–213°.

EXAMPLE 19

7-Hydroxy-2-(4-chlorobenzyl)-1,2,3,4-tetrahydroisoquinoline

Starting material for the preparation of compound 12.37 in Table 1

2.9 g of 7-hydroxyisoquinoline are heated under reflux for 8 hours with 3.5 g of 4-chlorobenzyl chloride in 30 ml of ethanol. After standing overnight, 5.7 g of the isoquinolinium salt crystallize out (melting point: 273°–274°). This salt is dissolved in 200 ml of methanol/water 9:1 and, with cooling, 6 g of sodium borohydride are added. After evolution of hydrogen has ended, the mixture is heated under reflux for 15 minutes. It is then concentrated to ⅓ of its volume, and this is poured into 200 ml of water, ammonium chloride is added to saturation, and the solid material which has precipitated out is filtered off. Recrystallization from ethanol gives 3.6 g of colorless crystals (67% of theory), melting point: 177°–178°.

EXAMPLE 20

6-Hydroxy-2-(4-chlorophenyl)-1,2,3,4-tetrahydroisoquinoline

Starting material for the preparation of compound 12.159 in Table 1

(a)

N-(4-Chlorophenyl)-2-(3-methoxyphenyl)ethylamine 22.1 g of N-(4-chlorophenyl)-3-methoxyphenylacetamide are reduced with lithium aluminum hydride in THF. After destroying the reagent with water, filtering, drying and evaporating in a rotary evaporator, the oily residue is taken up in diethyl ether, and the desired product is precipitated as the hydrochloride.

Yield: 16.6 g of colorless powder (70% of theory), melting point: 149°–150°.

(b)

2-(4-Chlorophenyl)-6-methoxy-1,2,3,4-tetrahydroisoquinoline 14.4 g of the product described under (a), 6 ml of 35% strength aqueous formaldehyde solution and 10 ml of concentrated hydrochloric acid in 20 ml of methanol are heated under reflux for 1 day. On distilling off the methanol, the product crystallizes out. After cooling, it is filtered off with suction and the resulting product (13.5 g, 91% of theory) is reacted further under (c) without further purification.

(c)

6-Hydroxy-2-(4-chlorophenyl)-1,2,3,4-tetrahydroisoquinoline 7.0 g of the compound prepared under (b) are heated under reflux for 8 hours with a mixture of 50 ml of glacial acetic acid/hydrobromic acid (48% strength) in the volume ratio 1:1. After removing the acid in a rotary evaporator, the residue is taken up with methylene chloride/dilute ammonia, and the organic phase is dried and evaporated in a rotary evaporator. The oily residue is chromatographed on silica gel using a mixture of methylene chloride/ethyl acetate in the ratio 19:1. 2.2 g of pale yellow crystals (38% of theory) are obtained, melting point: 122°–123°.

EXAMPLE 21

6-Hydroxy-2-acetyl-1,2,3,4-tetrahydroisoquinoline

Starting material for the preparation of compound 12.131 in Table 1

5.0 g of 6-hydroxy-1,2,3,4-tetrahydroisoquinoline are converted into the bisacetyl compound using acetic anhydride or acetyl chloride/triethylamine, and, without purification, this compound is heated under reflux for 6 hours with 10 ml of diethylamine in 50 ml of ethanol. The mixture is evaporated in vacuo in a rotary evaporator, and the residue is chromatographed on silica gel using ethyl acetate/methanol in the ratio 9:1. A yellow oil which crystallizes on trituration with diethyl ether is obtained. Yield: 5.2 g (78% of theory), melting point: 129°–130°.

EXAMPLE 22

6-Hydroxy-2-[3-(4-methoxyphenyl)propyl]-1,2,3,4-tetrahydroisoquinoline 5.4 g of 6-hydroxy-1,2,3,4-tetrahydroisoquinoline are acylated twice with 14.2 g of 4-methoxydihydrocinnamoyl chloride in methylene chloride in the presence of 7.5 g of triethylamine, the mixture is extracted by shaking with water, and the organic phase is dried and evaporated in a rotary evaporator. The crude product is dissolved, without further purification, in tetrahydrofuran, and added dropwise, with cooling, to a solution of 1.5 g of lithium aluminum hydride in dry tetrahydrofuran. After destroying the reagent with water, inorganic material is filtered off and the filtrate is dried. The residue from filtration is dried, extracted twice by boiling with methanol, and the methanol and tetrahydrofuran are evaporated together in a rotary evaporator. After triturating the oily residue with ethyl acetate, 3.5 g of colorless product (33% of theory) are obtained. Melting point: 163°–164°.

EXAMPLE 23

The following compounds of the general formula (III) listed in Table 2 can be prepared in analogy to Examples 13–22 by using equivalent amounts of the appropriate starting compounds.

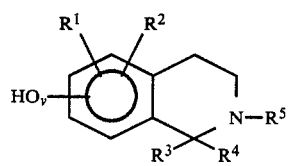

(III)

v = position of the hydroxyl group on the isoquinoline.

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.1 | 6 | H | H | C₂H₅ | H | CH₃ | | | 12.10 |
| 23.2 | 6 | H | H | CH₃ | CH₃ | CH₃ | | | 12.11 |
| 23.3 | 6 | H | H | —(CH₂)₅— | | CH₃ | | | 12.12 |
| 23.4 | 6 | H | H | —(CH₂)₂—O—(CH₂)₂— | | CH₃ | 98–100 | | 12.13 |
| 23.5 | 6 | H | H | —(CH₂)₂—N—(CH₂)₂<br>　　　　　CH₃ | | CH₃ | 175–177 | 18 | 12.14 |
| 23.6 | 6 | H | H | —(CH₂)₂—N₃—(CH₂)₂<br>　　　　　CH₂C₆H₅ | | CH₃ | Resin | 18 | 12.15 |
| 23.7 | 6 | H | H | —(CH₂)₂—N—(CH₂)₂—<br>　　　　　COCH₃ | | CH₃ | Resin | 18 | 12.16 |
| 23.8 | 6 | H | H | —(CH₂)₂—N—(CH₂)₂—<br>　　　　　COC₆H₅ | | CH₃ | 270° decomp. | 18 | 12.17 |
| 23.9 | 6 | H | H | —(CH₂)₂—N—(CH₂)₂—<br>　　　　　COOC₂H₅ | | CH₃ | 237–238 | 18 | 12.18 |
| 23.10 | 6 | H | H | ![Cl-phenyl] | H | CH₃ | Resin | 18 | 12.19 |
| 23.11 | 6 | H | H | ![2,4-diCl-phenyl] | H | CH₃ | 175 | 18 | 12.20 |
| 23.12 | 6 | H | H | ![CF₃-phenyl] | H | CH₃ | Resin | 18 | 12.21 |
| 23.13 | 6 | H | H | ![OCH₃-phenyl] | H | CH₃ | Resin | 18 | 12.22 |

-continued

| Compound No. | V | $R^1$ | $R^2$ | $R^3$ | $R^4$ | $R^5$ | Melting point (°C.) | Preparation in analogy to Example | Starting material for Example or Compound No. in Tab. 1 |
|---|---|---|---|---|---|---|---|---|---|
| 23.14 | 6 | H | H | 4-(N(CH$_3$)$_2$)-phenyl | H | CH$_3$ | Resin | 18 | 12.23 |
| 23.15 | 6 | H | H | 4-phenyl-phenyl | H | CH$_3$ | 230° decomp. | 18 | 12.24 |
| 23.16 | 6 | H | H | naphthyl | H | CH$_3$ | 160–162 | 18 | 12.25 |
| 23.17 | 6 | H | H | thienyl | H | CH$_3$ | 163–165 | 18 | 12.26 |
| 23.18 | 6 | 5-CH$_3$ | 7-CH$_3$ | H | H | CH$_3$ | 115–117 | 14 | 12.28 |
| 23.19 | 6 | H | H | H | H | -nC$_4$H$_9$ | | 17 | 12.29 |
| 23.20 | 6 | H | H | H | H | -nC$_{12}$H$_{25}$ | | 17 | 12.31 |
| 23.21 | 6 | H | H | H | H | -CH$_2$-CH=CH$_2$ | 142–145 | 14 | 2 |
| 23.22 | 6 | H | H | H | H | -CH$_2$-C≡CH | 173–174 | 14 | 12.32 |
| 23.23 | 6 | H | H | H | H | -CH$_2$-phenyl | 172–174 | 14 | 12.33 |
| 23.24 | 7 | H | H | H | H | -CH$_2$-phenyl | | 19 | 13.34 |
| 23.25 | 5 | H | H | H | H | -CH$_2$-(4-Cl-phenyl) | 181–182 | 19 | 12.35 |

-continued
| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.26 | 6 | H | H | H | H |  | 181–183 | 14 | 12.36, 12.38 |
| 23.27 | 6 | H | H | H | H |  | 253–255 | 15 | 12.39 |
| 23.28 | 7 | H | H | H | H |  | | 15 | 12.40 |
| 23.29 | 6 | H | H | H | H | 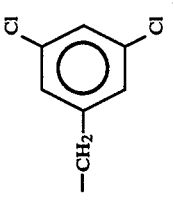 | | 14 | 12.41 |
| 23.30 | 6 | H | H | H | H | 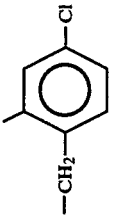 | 160–162 | 16 | 12.42 |
| 23.31 | 6 | H | H | H | H | 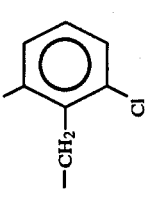 | | 16 | 12.43 |
| 23.32 | 6 | H | H | H | H | 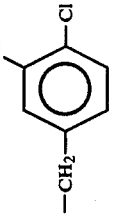 | | 14 | 12.44 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.33 | 6 | H | H | H | H | —CH₂—C₆H₄—Br | | 14 | 12.45 |
| 23.34 | 7 | H | H | H | H | —CH₂—C₆H₄—Br | | 19 | 12.46 |
| 23.35 | 7 | H | H | H | H | —CH₂—C₆H₄—F | 141–142 | 19 | 12.47 |
| 23.36 | 6 | H | H | H | H | —CH₂—C₆H₄—CH₃ | 156–158 | 16 | 12.48 |
| 23.37 | 6 | H | H | H | H | —CH₂—C₆H₄—OCH₃ | | 15 | 12.49 |
| 23.38 | 7 | H | H | H | H | —CH₂—C₆H₄—OCH₃ | | 15 | 12.50 |
| 23.39 | 6 | H | H | H | H | —CH₂—C₆H₄—N(CH₃)₂ | 194–195 | 15 | 12.51 |
| 23.40 | 7 | H | H | H | H | —CH₂—C₆H₄—N(CH₃)₂ | | 15 | 12.52 |

-continued
| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.41 | 6 | H | H | H | H | 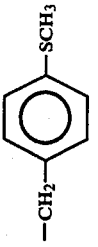 | 203–204 | 15 | 12.53 |
| 23.42 | 7 | H | H | H | H | 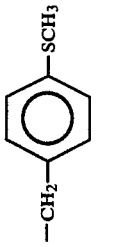 | | 15 | 12.54 |
| 23.43 | 6 | H | H | H | H | 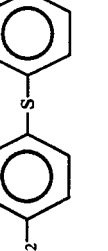 | 196–198 | 15 | 12.55 |
| 23.44 | 6 | H | H | H | H | 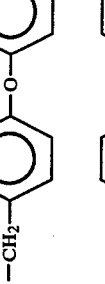 | | 15 | 12.56 |
| 23.45 | 7 | H | H | H | H | 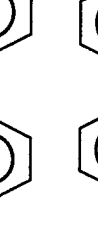 | | 15 | 12.57 |
| 23.46 | 6 | 5-CH₃ | 7-CH₃ | H | H | 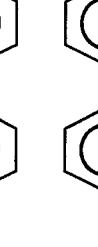 | 178–180 | 14 | 12.60 |
| 23.47 | 6 | 7-OCH₃ | H | H | H | 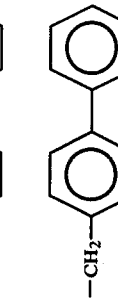 | 173–175 | 14 | 12.61 |
| 23.48 | 7 | H | H | H | H |  | 217–219 | 19 | 12.59 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.49 | 7 | H | H | H | H | —CH₂-(thiophen-2-yl) | | 15 | 12.63 |
| 23.50 | 6 | H | H | H | H | —CH₂-(thiophen-3-yl) | 162 | 15 | 12.64 |
| 23.51 | 7 | H | H | H | H | —CH₂-(thiophen-3-yl) | | 15 | 12.65 |
| 23.52 | 6 | H | H | H | H | —CH₂-(furan-2-yl) | Resin | 15 | 12.66 |
| 23.53 | 7 | H | H | H | H | —CH₂-(furan-2-yl) | | 15 | 12.67 |
| 23.54 | 6 | H | H | H | H | —CH₂-(pyridin-4-yl) | 200–203 | 14 | 12.68 |
| 23.55 | 6 | H | H | H | H | —CH₂-(naphthyl) | 217–218 | 14 | 12.69 |
| 23.56 | 7 | H | H | H | H | —CH₂-(naphthyl) | | 19 | 12.70 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.57 | 6 | H | H | H | H | —CH₂—CH₂—C₆H₅ | | 17 | 12.72 |
| 23.58 | 7 | H | H | H | H | —CH₂—CH₂—C₆H₅ | | 17 | 12.73 |
| 23.59 | 6 | H | H | H | H | —CH₂—CH₂—C₆H₄(4-Cl) | 181–182 | 17 | 12.74, 11.75, 12.76 |
| 23.60 | 7 | H | H | H | H | —CH₂—CH₂—C₆H₄(4-Cl) | 191–192 | 17 | 12.77 |
| 23.61 | 6 | H | H | H | H | —CH₂—CH₂—C₆H₄(4-OCH₃) | 180–183 | 22 | 9 |
| 23.62 | 7 | H | H | H | H | —CH₂—CH₂—C₆H₄(4-OCH₃) | | 22 | 12.78 |
| 23.63 | 6 | H | H | H | H | —CH₂—CH₂—C₆H₃(3,4-(OCH₃)₂) | | 22 | 12.79 |
| 23.64 | 6 | H | H | H | H | —CH₂—CH₂—C₆H₄(3-CF₃) | | 17 | 12.80 |

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.65 | 6 | H | H | H | H | —CH₂—CH₂—C₆H₄—F | | 17 | 12.81 |
| 23.66 | 7 | H | H | H | H | —CH₂—CH₂—C₆H₄—F | | 17 | 12.82 |
| 23.67 | 7 | H | H | H | H | —CH₂—CH₂-biphenyl | | 17 | 12.83 |
| 23.68 | 6 | H | H | H | H | —CH₂—CH₂-naphthyl | | 17 | 12.84 |
| 23.69 | 6 | H | H | H | H | —CH₂—CH₂-(dihydrothiophene) | | 17 | 12.85 |
| 23.70 | 7 | H | H | H | H | —CH₂—CH₂-(dihydrothiophene) | | 17 | 12.86 |
| 23.71 | 6 | H | H | H | H | —CH₂—CH₂-(thiophene) | | 17 | 12.87 |
| 23.72 | 7 | H | H | H | H | —CH₂—CH₂-(thiophene) | | 17 | 12.88 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.73 | 6 | H | H | H | H | −CH₂−CH₂−(3-pyridyl) | | 17 | 12.89 |
| 23.74 | 6 | H | H | H | H | −(CH₂)₃−phenyl | | 17 | 12.90 |
| 23.75 | 7 | H | H | H | H | −(CH₂)₃−phenyl | | 17 | 12.91 |
| 23.76 | 6 | H | H | H | H | −(CH₂)₃−(4-Cl-phenyl) | 164−166 | 17 | 12.92, 12.93 |
| 23.77 | 7 | H | H | H | H | −(CH₂)₃−(4-Cl-phenyl) | | 17 | 12.94 |
| 23.78 | 6 | H | H | H | H | −(CH₂)₃−(4-F-phenyl) | | 17 | 12.95 |
| 23.79 | 7 | H | H | H | H | −(CH₂)₃−(4-F-phenyl) | | 17 | 12.96 |
| 23.80 | 6 | H | H | H | H | −(CH₂)₃−(4-CF₃-phenyl) | | 17 | 12.97 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.81 | 7 | H | H | H | H | —(CH₂)₃—C₆H₄—CF₃ | | 17 | 12.098 |
| 23.82 | 7 | H | H | H | H | —(CH₂)₃—C₆H₄—OCH₃ | | 22 | 12.100 |
| 23.83 | 6 | H | H | H | H | —(CH₂)₃-(2-thienyl) | | 17 | 12.101 |
| 23.84 | 7 | H | H | H | H | —(CH₂)₃-(2-thienyl) | | 17 | 12.102 |
| 23.85 | 6 | H | H | H | H | —(CH₂)₃-(3-thienyl) | | 17 | 12.103 |
| 23.86 | 7 | H | H | H | H | —(CH₂)₃-(3-thienyl) | | 17 | 12.104 |
| 23.87 | 6 | H | H | H | H | —(CH₂)₃-(4-pyridyl) | | 17 | 12.105 |
| 23.88 | 6 | H | H | H | H | —(CH₂)₄—C₆H₅ | | 17 | 12.106 |
| 23.89 | 7 | H | H | H | H | —(CH₂)₄—C₆H₅ | | 17 | 12.107 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.90 | 6 | H | H | H | H | —(CH₂)₄—C₆H₄—Cl | 164–166 | 17 | 12.108 |
| 23.91 | 7 | H | H | H | H | —(CH₂)₄—C₆H₄—Cl | | 17 | 12.109 |
| 23.92 | 6 | H | H | H | H | —(CH₂)₄—C₆H₄—OCH₃ | | 22 | 12.110 |
| 23.93 | 7 | H | H | H | H | —(CH₂)₄—C₆H₄—OCH₃ | | 22 | 12.111 |
| 23.94 | 6 | H | H | H | H | —(CH₂)₄—C₆H₄—F | | 17 | 12.112 |
| 23.95 | 7 | H | H | H | H | —(CH₂)₄—C₆H₄—F | | 17 | 12.113 |
| 23.96 | 6 | H | H | H | H | —(CH₂)₄—C₆H₄—C₆H₅ | | 17 | 12.114 |
| 23.97 | 7 | H | H | H | H | —(CH₂)₄—C₆H₄—C₆H₅ | | 17 | 12.115 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.98 | 6 | H | H | H | H | —(CH₂)₄—(2-thienyl) | | 17 | 12.116 |
| 23.99 | 7 | H | H | H | H | —(CH₂)₅—(2-thienyl) | | 17 | 12.117 |
| 23.100 | 6 | H | H | H | H | —(CH₂)₅—phenyl | | 17 | 12.118 |
| 23.101 | 7 | H | H | H | H | —(CH₂)₅—phenyl | | 17 | 12.119 |
| 23.102 | 6 | H | H | H | H | —(CH₂)₅—(4-Cl-phenyl) | | 17 | 12.120 |
| 23.103 | 7 | H | H | H | H | —(CH₂)₅—(4-Cl-phenyl) | | 17 | 12.121 |
| 23.104 | 6 | H | H | H | H | —(CH₂)₅—(4-OCH₃-phenyl) | | 22 | 12.122 |
| 23.105 | 7 | H | H | H | H | —(CH₂)₅—(4-OCH₃-phenyl) | | 22 | 12.123 |
| 23.106 | 6 | H | H | H | H | —(CH₂)₅—(4-F-phenyl) | | 17 | 12.124 |

-continued

| Compound No. | V | $R^1$ | $R^2$ | $R^3$ | $R^4$ | $R^5$ | Melting point (°C.) | Preparation in analogy to Example | Starting material for Example or Compound No. in Tab. 1 |
|---|---|---|---|---|---|---|---|---|---|
| 23.107 | 7 | H | H | H | H | —(CH$_2$)$_5$—C$_6$H$_4$—F | | 17 | 12.125 |
| 23.108 | 6 | H | H | H | H | —(CH$_2$)$_5$—C$_6$H$_4$—C$_6$H$_5$ | | 17 | 12.126 |
| 23.109 | 7 | H | H | H | H | —(CH$_2$)$_5$—C$_6$H$_4$—C$_6$H$_5$ | | 17 | 12.127 |
| 23.110 | 6 | H | H | H | H | —(CH$_2$)$_5$-(tetrahydrothiophene) | | 17 | 12.128 |
| 23.111 | 7 | H | H | H | H | —(CH$_2$)$_5$-(tetrahydrothiophene) | | 17 | 12.129 |
| 23.112 | 7 | H | H | H | H | —COCH$_3$ | | 21 | 12.132 |
| 23.113 | 6 | H | H | H | H | —CO—C$_6$H$_5$ | | 13 | 12.133 |
| 23.114 | 7 | H | H | H | H | —CO—C$_6$H$_5$ | | 13 | 12.134 |
| 23.115 | 7 | H | H | H | H | —CO—C$_6$H$_4$—Cl | | 13 | 12.136 |

-continued
| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.116 | 6 | H | H | H | H |  | | 13 | 12.137 |
| 23.117 | 7 | H | H | H | H |  | | 13 | 12.138 |
| 23.118 | 6 | H | H | H | H |  | | 13 | 12.139 |
| 23.119 | 7 | H | H | H | H |  | | 13 | 12.140 |
| 23.120 | 6 | H | H | H | H |  | | 13 | 12.141 |
| 23.121 | 7 | H | H | H | H |  | | 13 | 12.142 |
| 23.122 | 6 | H | H | H | H |  | | 13 | 12.143 |
| 23.123 | 7 | H | H | H | H |  | | 13 | 12.144 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.124 | 6 | H | H | H | H | 3,4,5-tri-OCH₃-C₆H₂-CO- | | 13 | 12.145 |
| 23.125 | 7 | H | H | H | H | 3,4,5-tri-OCH₃-C₆H₂-CO- | | 13 | 12.146 |
| 23.126 | 6 | H | H | H | H | 4-N(CH₃)₂-C₆H₄-CO- | 244–247 | 13 | 12.147 |
| 23.127 | 7 | H | H | H | H | 4-N(CH₃)₂-C₆H₄-CO- | | 13 | 12.148 |
| 23.128 | 6 | H | H | H | H | 4-CH₃-C₆H₄-CO- | | 13 | 12.149 |
| 23.129 | 7 | H | H | H | H | 4-CH₃-C₆H₄-CO- | | 13 | 12.150 |
| 23.130 | 6 | H | H | H | H | 2-thienyl-CO- | | 13 | 12.151 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.131 | 7 | H | H | H | H | ![thiophene-CO-] | | 13 | 12.152 |
| 23.132 | 6 | H | H | H | H | ![furan-CO-] | | 13 | 12.153 |
| 23.133 | 7 | H | H | H | H | ![furan-CO-] | | 13 | 12.154 |
| 23.134 | 6 | H | H | H | H | ![pyridine-CO-] | | 13 | 12.155 |
| 23.135 | 7 | H | H | H | H | ![pyridine-CO-] | | 13 | 12.156 |
| 23.136 | 6 | H | H | H | H | ![pyridine-CO-] | | 13 | 12.157 |
| 23.137 | 7 | H | H | H | H | ![pyridine-CO-] | | 13 | 12.158 |
| 23.138 | 6 | H | H | H | H | ![4-F-phenyl] | | 20 | 12.159 |
| 23.139 | 6 | H | H | H | H | ![4-Br-phenyl] | | 20 | 12.161 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.140 | 6 | H | H | H | H | 4-CH₃-C₆H₄ | | 20 | 12.162 |
| 23.141 | 6 | H | H | H | H | 4-CF₃-C₆H₄ | | 20 | 12.163 |
| 23.142 | 6 | H | H | H | H | 3,5-Cl₂-C₆H₃ | | 20 | 12.164 |
| 23.143 | 6 | H | H | H | H | 2,4-Cl₂-C₆H₃ | | 20 | 12.165 |
| 23.144 | 6 | H | H | H | H | 4-N(CH₃)₂-C₆H₄ | | 20 | 12.166 |
| 23.145 | 6 | H | H | H | H | 4-C₆H₅-C₆H₄ | | 20 | 12.167 |
| 23.146 | 6 | H | H | H | H | C₆H₅ | | 20 | 12.168 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.147 | 6 | H | H | H | H | —CH₂—⟨phenyl with OCH₃, OCH₃⟩ | | 15 | 12.169 |
| 23.148 | 7 | H | H | H | H | —CH₂—⟨phenyl with OCH₃, OCH₃⟩ | | 15 | 12.170 |
| 23.149 | 6 | H | H | H | H | —CH₂—⟨phenyl with OCH₃, OCH₃, OCH₃⟩ | 215–217 | 15 | 12.171 |
| 23.150 | 7 | H | H | H | H | —CH₂—⟨phenyl with OCH₃, OCH₃, OCH₃⟩ | | 15 | 12.172 |
| 23.151 | 6 | H | H | H | H | —CH₂—CH₂—⟨phenyl with CF₃⟩ | | 17 | 12.173 |
| 23.152 | 7 | H | H | H | H | —CH₂—CH₂—⟨phenyl with CF₃⟩ | | 17 | 12.174 |
| 23.153 | 6 | H | H | H | H | —CH₂—⟨phenyl with NO₂⟩ | | 14 | 12.175 |

-continued
| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.154 | 7 | H | H | H | H | —CH₂—C₆H₄—NO₂ (p)  | | 14 | 12.176 |
| 23.155 | 6 | H | H | H | H | —CH₂—C₆H₄—NO₂ (m)  | | 14 | 12.177 |
| 23.156 | 7 | H | H | H | H | —CH₂—C₆H₄—NO₂ (m) 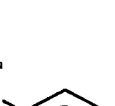 | | 14 | 12.178 |
| 23.157 | 6 | H | H | H | H | —CH₂—CH₂—C₆H₄—NO₂ (p) 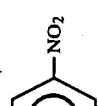 | | 16 | 12.179 |
| 23.158 | 7 | H | H | H | H | —CH₂—CH₂—C₆H₄—NO₂ (p) 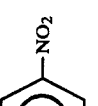 | | 16 | 12.180 |
| 23.159 | 6 | H | H | H | H | —CH₂—CH₂—C₆H₄—NO₂ (m) 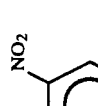 | | 16 | 12.181 |
| 23.160 | 7 | H | H | H | H | —CH₂—CH₂—C₆H₄—NO₂ (m) 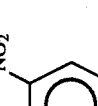 | | 16 | 12.182 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.161 | 6 | H | H | H | H | —(CH₂)₃—C₆H₄—NO₂ (para) | | 16 | 12.183 |
| 23.162 | 7 | H | H | H | H | —(CH₂)₃—C₆H₄—NO₂ (para) | | 16 | 12.184 |
| 23.163 | 6 | H | H | H | H | —(CH₂)₃—C₆H₄—NO₂ (meta) | | 16 | 12.185 |
| 23.164 | 7 | H | H | H | H | —(CH₂)₃—C₆H₄—NO₂ (meta) | | 16 | 12.186 |
| 23.165 | 7 | H | H | H | H | —CH₂—C₆H₃(Cl)₂ (3,5) | | 14 | 12.187 |
| 23.166 | 7 | H | H | H | H | —CH₂—C₆H₄—Cl (para) | | 14 | 12.188 |
| 23.167 | 7 | H | H | H | H | —CH₂—C₆H₃(Cl)(OCH₃) | | 14 | 12.189 |

-continued

| Compound No. | V | R¹ | R² | R³ | R⁴ | R⁵ | Melting point (°C.) | Preparation in analogy to Example | Starting material for Example or Compound No. in Tab. 1 |
|---|---|---|---|---|---|---|---|---|---|
| 23.168 | 7 | H | H | H | H | —CH₂—(2,4-Cl,CF₃-phenyl) | | | 12.190 |
| 23.169 | 7 | H | H | H | H | —(CH₂)₃—(pyridyl) | | 17 | 12.191 |
| 23.170 | 6 | H | H | H | H | —CO—(pyridyl) | | 13 | 12.192 |
| 23.171 | 7 | H | H | H | H | —C(=O)—(pyridyl) | | 13 | 12.193 |

We claim:
1. A 1-(1,3-dioxolan-2-ylmethyl)azole of the formula I

or a stereoisomer thereof or a salt thereof with a physiologically tolerated acid, in which G denotes a 1-(1,3-dioxolan-2-ylmethyl)azole radical of the structure

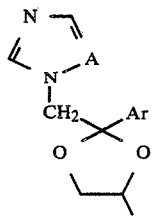

in which A denotes nitrogen or methine, Ar denotes naphthyl, biphenylyl, thienyl, or a phenyl group which is unsubstituted or bears one, two or three substituents, the substituents being identical or different and denoting fluorine, chlorine, bromine, iodine, trifluoromethyl, $C_1$-$C_4$-alkyl or $C_1$-$C_4$-alkoxy, and D in formula I denotes either (a) an isoquinoline group of the formula D I

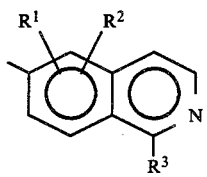

where $R^1$ and $R^2$, independently of one another, denote a hydrogen atom, fluorine, chlorine, bromine, iodine, $C_1$-$C_4$-alkyl or $C_1$-$C_4$-alkoxy, and $R^3$ denotes a hydrogen atom, $C_1$-$C_{12}$-alkyl, $C_3$-$C_8$-cycloalkyl, $C_3$-$C_5$-alkenyl, $C_3$-$C_5$-alkinyl, trifluoromethyl, trichloromethyl, an aryl group selected from phenyl, naphthyl and biphenylyl groups, an aryl-($C_1$-$C_5$-alkyl) group wherein said aryl is selected from phenyl, naphthyl and biphenylyl groups, a heteroaryl group selected from thienyl, furyl and pyridyl groups, a heteroaryl-($C_1$-$C_5$-alkyl) group wherein said heteroaryl is selected from thienyl, furyl and pyridyl groups, and wherein said aryl, aryl-($C_1$-$C_5$-alkyl), heteroaryl and heteroaryl-($C_1$-$C_5$-alkyl) groups may be unsubstituted or may bear one, two or three substituents, said substituents being identical or different, and each denoting fluorine, chlorine, bromine, iodine, nitro, $C_1$-$C_4$-alkyl, trifluoromethyl, $C_1$-$C_4$-alkoxy, $C_1$-$C_4$-alkylthio, $C_1$-$C_4$-dialkylamino wherein the alkyl groups in said $C_1$-$C_4$-dialkylamino are separate or form together with the nitrogen atom to which they are attached a pyrrolidine, piperidine or hexamethylene imine ring, phenylthio, halogenophenylthio, phenoxy or halogenophenoxy, or (b) denotes a 3,4-dihydroisoquinoline group of the formula D II

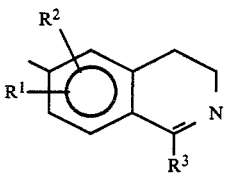

where $R^1$, $R^2$ and $R^3$ have the meanings indicated for formula D I, or (c) denotes a 1,2,3,4-tetrahydroisoquinoline group of the formula D III

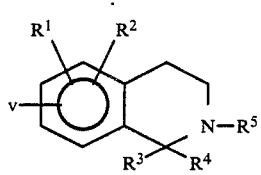

where v indicates the position of linkage of the isoquinoline system to the G-CH$_2$-O radical, $R^1$, $R^2$ and $R^3$ have the meanings indicated for formula D I, and $R^4$ denotes a hydrogen atom or a $C_1$-$C_4$-alkyl group, and additionally, if $R^3$ and $R^4$ are alkyl groups, these, together with the carbon atom bearing them, can denote a spirocyclic ring system of the formula D III'

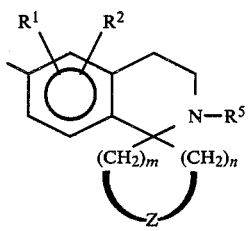

in which m and n denote 1, 2 or 3, and z denotes either a methylene group or, if m=n=2, a heteroatom from the group consisting of oxygen, sulphur and nitrogen, the nitrogen being unsubstituted or substituted by a radical $R^6$ which denotes $C_1$-$C_4$-alkyl, $C_1$-$C_5$-alkanoyl, $C_1$-$C_4$-alkoxycarbonyl, or a benzoyl or benzyl group which is unsubstituted or bears one or two substituents, the substituents on the benzoyl or benzyl group being identical or different and each denoting fluorine, chlorine, bromine, iodine, $C_1$-$C_4$-alkyl, trifluoromethyl or $C_1$-$C_4$-alkoxy and, when $R^3$ and/or $R^4$ is not a hydrogen atom, v denotes the 6-position, or, when $R^3$ and $R^4$ are hydrogen atoms, v denotes the 5-, 6-, 7- or 8-position, and, if $R^3$ and/or $R^4$ is not a hydrogen atom, $R^5$ denotes a hydrogen atom or a $C_1$-$C_4$-alkyl group, or, if $R^3$ and $R^4$ are hydrogen atoms and v denotes the 5-, 7- or 8-position, $R^5$ has the meanings indicated for $R^3$ in formula D I, with the proviso that $R^5$ does not denote an aryl or heteroaryl group, or, when $R^3$ and $R^4$ are hydrogen atoms and v denotes the 6-position, $R^5$ has the meanings indicated for $R^3$ in formula D I, and $R^5$ also denotes an acyl group of the formula Q,

 (Q)

where $R^7$ has the meanings indicated for $R^3$ in the formula D I.

2. A pharmaceutical formulation which contains from 50 to 200 mg of a compound of the formula I or a stereoisomer or a salt thereof as claimed in claim 1 and a pharmaceutically acceptable carrier.

3. A method of treating a mammal for controlling mycoses, protozoa and Gram-positive and Gram-negative bacteria which comprises administering to said mammal daily doses of 50–200 mg of a compound of the formula I or a stereoisomer or a salt thereof as claimed in claim 1.

* * * * *